United States Patent
Sato et al.

(10) Patent No.: US 7,449,513 B2
(45) Date of Patent: *Nov. 11, 2008

(54) ALKENYL ETHER COMPOUND, POLYMER COMPOUND, COMPOSITION USING THEM, AND IMAGE FORMATION METHOD AND APPARATUS

(75) Inventors: Koichi Sato, Atsugi (JP); Ikuo Nakazawa, Zama (JP); Sakae Suda, Sagamihara (JP); Masayuki Ikegami, Atsugi (JP); Keiichiro Tsubaki, Kawasaki (JP); Ryuji Higashi, Atsugi (JP); Keiko Yamagishi, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 369 days.

This patent is subject to a terminal disclaimer.

(21) Appl. No.: 10/540,946

(22) PCT Filed: Apr. 30, 2004

(86) PCT No.: PCT/JP2004/006348

§ 371 (c)(1), (2), (4) Date: Jun. 29, 2005

(87) PCT Pub. No.: WO2004/099264

PCT Pub. Date: Nov. 18, 2004

(65) Prior Publication Data

US 2006/0178468 A1    Aug. 10, 2006

(30) Foreign Application Priority Data

| May 8, 2003 | (JP) | ............................. 2003-129997 |
| Aug. 29, 2003 | (JP) | ............................. 2003-307618 |
| Apr. 26, 2004 | (JP) | ............................. 2004-130295 |

(51) Int. Cl.
  C08L 31/00 (2006.01)
  C07C 69/73 (2006.01)
  C08C 59/40 (2006.01)
  C08F 16/26 (2006.01)

(52) U.S. Cl. ............... 524/556; 526/317.1; 526/319; 526/333; 526/271; 526/279; 523/160; 523/161; 560/183

(58) Field of Classification Search ............... 524/556; 526/317.1, 319, 333, 271, 279; 560/183; 523/160, 161

See application file for complete search history.

(56) References Cited

U.S. PATENT DOCUMENTS

| 4,313,124 A | 1/1982 | Hara .................... 346/140 R |
| 4,345,262 A | 8/1982 | Shirato et al. ............ 346/140 R |
| 4,459,600 A | 7/1984 | Sato et al. .............. 346/140 R |
| 4,463,359 A | 7/1984 | Ayata et al. ................ 346/1.1 |
| 4,558,333 A | 12/1985 | Sugitani et al. .......... 346/140 R |
| 4,723,129 A | 2/1988 | Endo et al. ................ 346/1.1 |
| 4,740,796 A | 4/1988 | Endo et al. ................ 346/1.1 |
| 4,758,348 A | 7/1988 | Matsui et al. ............... 210/651 |
| 5,085,698 A | 2/1992 | Ma et al. ..................... 106/20 |
| 5,169,983 A | 12/1992 | Fielding et al. ............... 562/56 |
| 5,897,940 A | 4/1999 | Malhotra ..................... 428/212 |
| 2005/0033010 A1 | 2/2005 | Sato et al. ..................... 528/80 |
| 2005/0131102 A1 | 6/2005 | Nakazawa et al. .......... 523/160 |
| 2005/0140762 A1 | 6/2005 | Sato et al. ..................... 347/100 |
| 2005/0197424 A1 | 9/2005 | Higashi et al. .............. 523/160 |
| 2005/0219277 A1 | 10/2005 | Sato et al. ....................... 347/1 |
| 2005/0239918 A1 | 10/2005 | Nakazawa et al. .......... 523/160 |
| 2005/0249925 A1 | 11/2005 | Ikegami et al. ........... 428/195.1 |
| 2006/0004124 A1 | 1/2006 | Tsubaki et al. .............. 523/160 |

(Continued)

FOREIGN PATENT DOCUMENTS

EP    1357138 A1 * 10/2003

(Continued)

OTHER PUBLICATIONS

V. Percec and H. Oda "Molecular Engineering of Liquid-crystalline Polymers of Living" Polymerization. Part 31. Synthesis and 'living' cationic polymerization of (2R, 3S)-2-fluoro-3-methylpentyl 3-fluoro-4'- (ω-vinyloxyalkoxy) biphenyl-4-carboxylate with undecanyl and octyl alkyl groups, J. Mater. Chem., 1995, 5(8), 1125-1136.*

(Continued)

*Primary Examiner*—Randy Gulakowski
*Assistant Examiner*—Michael M Bernshteyn
(74) *Attorney, Agent, or Firm*—Fitzpatrick, Cella, Harper & Scinto

(57) ABSTRACT

A polymer compound is provided which is suitable to improve the dispersibility of coloring materials or solids in an ink or toner composition and which has a repeating unit represented by the general formula (2): (2) wherein X' represents a polyalkenyl group; each A represents independently a linear or branched alkylene group of 1 to 15 carbon atoms which may be substituted; m represents an integer of 0 to 30; B represents a single bond or an alkylene group which may be substituted; each D represents independently an aromatic ring in which at least one hydrogen atom attached to the ring is displaced by a fluorine atom; n represents an integer of 1 to 10; and R represents a hydrogen atom, an alkyl group which may be substituted, or an aromatic ring which may be substituted.

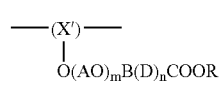

4 Claims, 2 Drawing Sheets

U.S. PATENT DOCUMENTS

2006/0100310 A1  5/2006  Nakazawa et al. .......... 523/160
2006/0128828 A1  6/2006  Sato et al. .................. 523/160

FOREIGN PATENT DOCUMENTS

| JP | 59-123670 | 7/1984 |
| JP | 59-138461 | 8/1984 |
| JP | 11-322866 | 11/1999 |
| JP | 11-322942 | 11/1999 |

OTHER PUBLICATIONS

V. Percec and H. Oda "Molecular Engineering of Liquid-crystalline Polymers of 'Living' Polymerization. Part 31. Synthesis and 'living' cationic polymerization of (2R, 3S)-2-fluoro-3-methylpentyl 3-fluoro-4'- (vinyloxyalkoxy) biphenyl-4-carboxylate with undecanyl and octyl alkyl groups", J. Mater. Chem., 1995, 5(8), 1125-1136.*

Takeuchi et al., "Living Cationic Polymerization of Ethyl 2-(Vinyloxy)ethoxyacetate: A Vinyl Ether with an Ether and an Ester Function in the Pendant," Journal of Polymer Science: Part A: Polymer Chemistry, vol. 27, 3303-3314 (1989).

Sadahito Aoshima et al., "Living Cationic Polymerization of Vinyl Monomers by Organoaluminium Halides," Polymer Bulletin, vol. 15, No. 5, May 1986, pp. 417-423.

* cited by examiner

ALKENYL ETHER COMPOUND, POLYMER COMPOUND, COMPOSITION USING THEM, AND IMAGE FORMATION METHOD AND APPARATUS

TECHNICAL FIELD

The present invention relates to a novel alkenyl ether compound useful as various types of functional material, a polymer compound, a composition using them, and an image formation method and apparatus using the above composition. Particularly preferably, it relates to an ink composition and a toner composition in which these compounds are used with a solvent or dispersion medium and a coloring material, and an image formation method and apparatus using these compositions.

BACKGROUND ART

Aqueous dispersion materials containing a functional substance have conventionally been known widely as functional materials, such as agricultural chemicals such as herbicides or insecticides, pharmaceuticals such as antitumor agents, antiallergic agents or antiphlogistics, and coloring materials such as ink or toner containing a coloring agent. In particular, coloring materials are dissolved or dispersed, so as to prepare an ink composition or toner composition. "Journal of Polymer Science Part A, Polymer Chemistry" Vol. 27, pp. 3303 to 3314, 1989 discloses a preferred use of various polymer materials, in which vinyl polymers such as styryl, acryl or methacryl polymers are used. With regard to a coloring material composition comprising a solvent or water as a base material, an attempt has generally been made that a polymer material preferably comprising an ionic functional group is used, so as to improve dispersibility of coloring materials such as pigments. In addition, using such toner compositions or ink compositions, digital printing techniques have been highly developed in recent years. Electrophotography and ink-jet technique are representative examples of such digital printing techniques, and in these years, the presence of such techniques have been increasingly enhanced as image formation techniques applied both in office and home.

Among others, the ink-jet technique is a direct recording method characterized in that it is compact in scale, resulting in low power consumption. In addition, image quality is being rapidly improved by miniaturization of nozzles or the like. Examples of such ink-jet techniques include a method comprising heating an ink supplied from an ink tank with a heater in a nozzle so as to evaporate the ink and form an ink bubble, and then ejecting the ink bubble to form an image oh a recording medium. Another example is a method of vibrating piezo elements to elect an ink from a nozzle. Since an aqueous dye solution has been commonly used as ink used in these methods, there have been some cases where smearing has been occurred, or a phenomenon called feathering has been appeared in the fiber direction of paper at a recording area on a recording medium, when different colors were overlaid. U.S. Pat. No. 5,085,698 describes that the use of pigment dispersion ink has been studied to improve the above problems. However, it is still desired that many other improvements have been made for such ink.

DISCLOSURE OF THE INVENTION

The present invention has been accomplished under the above-described circumstances and provides a polymer compound and a block polymer preferably used to improve the dispersibility of functional substances.

Moreover, the present invention provides a functional composition using the above polymer or block polymer, and in particular, a recording material such as an ink composition or toner composition, and an image formation method, a liquid application method and an apparatus using the above compositions.

The present inventors have conducted intensive studies regarding the above prior art techniques and problems, thereby completing the present invention described below.

The present invention provides an alkenyl ether compound comprising at least one of an aromatic carboxylic acid having a fluorine atom and an aromatic carboxylic acid ester having a fluorine atom, which is preferably represented by the general formula (1):

$$XO(AO)_m B(D)_n COOR \quad (1)$$

wherein X represents an alkenyl group; each A represents independently a linear or branched alkylene group of 1 to 15 carbon atoms which may be substituted; m represents an integer of 0 to 30; B represents a single bond or an alkylene group which may be substituted; each D represents independently an aromatic ring in which at least one hydrogen atom attached to the ring is replaced by a fluorine atom; n represents an integer of 1 to 10; and R represents a hydrogen atom, an alkyl group which may be substituted, or an aromatic ring which may be substituted.

Moreover, the present invention provides a polymer compound comprising a polyalkenyl ether repeating unit comprising at least one selected from a carboxylic acid, a carboxylic acid ester and a carboxylic acid salt, each having a fluorine atom in a side chain thereof, which preferably has a repeating unit represented by the general formula (2) or (3):

(2)

wherein X' represents a polyalkenyl group; each A represents independently a linear or branched alkylene group of 1 to 15 carbon atoms which may be substituted; m represents an integer of 0 to 30; B represents a single bond or an alkylene group which may be substituted; each D represents independently an aromatic ring in which at least one hydrogen atom attached to the ring is displaced by a fluorine atom; n represents an integer of 1 to 10; and R represents a hydrogen atom, an alkyl group which may be substituted, or an aromatic ring which may be substituted; or

(3)

wherein X' represents a polyalkenyl group; each A represents independently a linear or branched alkylene group of 1 to 15 carbon atoms which may be substituted; m represents an integer of 0 to 30; B represents a single bond or an alkylene group which may be substituted; each D represents independently an aromatic ring in which at least one hydrogen atom attached to the ring is displaced by a fluorine atom; n represents an integer of 1 to 10; and M represents a monovalent or polyvalent metal cation.

Furthermore, the present invention provides a block polymer which comprises a polyalkenyl ether repeating unit comprising an aromatic structure having a fluorine atom in a side chain thereof in at least one block segment, wherein the aromatic structure is at least one selected from a carboxylic acid, a carboxylic acid ester and a carboxylic acid salt.

Still further, the present invention provides a composition which comprises a solvent or dispersion medium, a functional substance, and the polymer compound or block polymer in accordance with the present invention.

Still further, the present invention provides an image recording method that comprises the steps of preparing the composition in accordance with the present invention and recording the composition on a medium.

Still further, the present invention provides an image recording apparatus that comprises a recording means for recording the composition in accordance with the present invention on a medium.

By polymerizing the novel polymeric compound of the present invention, it is possible to provide a polymer compound that is preferably used to prepare an ink or toner composition in which coloring materials or solids are well dispersed.

Further, by mixing the polymer compound of the invention with a solvent or a dispersing medium and a coloring material, it is possible to provide a composition such as an ink or toner composition, and a recording material.

Moreover, it is possible to provide a variety of image forming methods and apparatuses that employ recording materials such as ink or toner compositions using the polymer of the present invention.

BEST MODE FOR CARRYING OUT THE INVENTION

Figure 1:
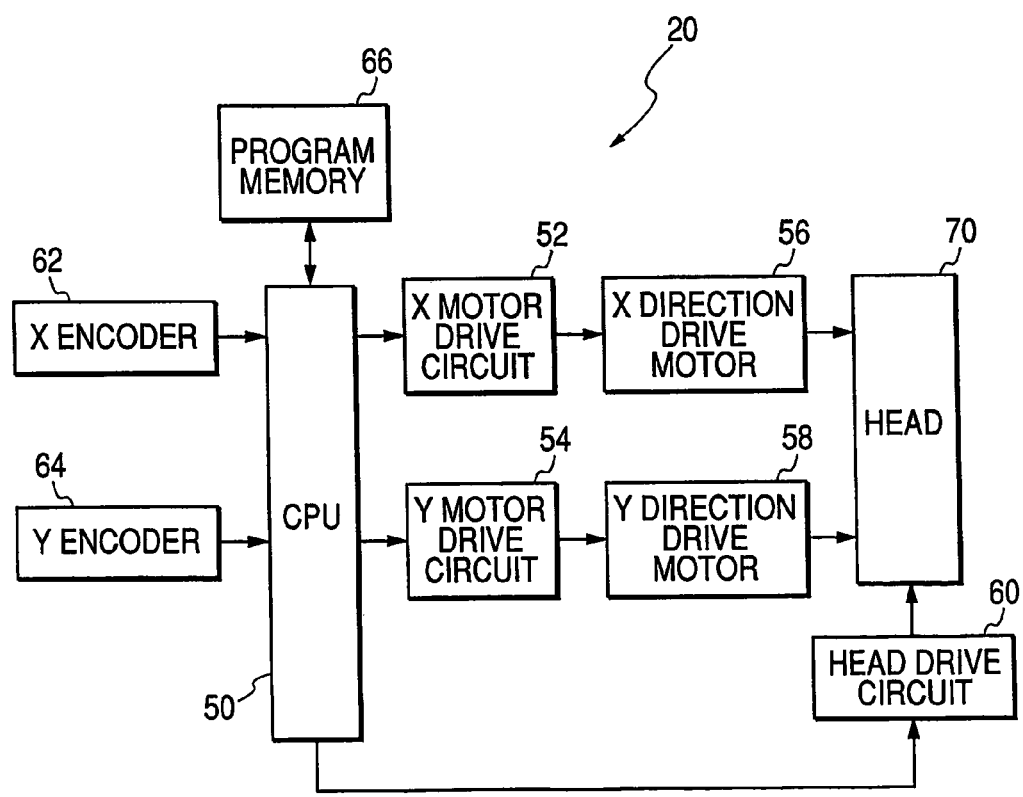
FIG. 1 is a block diagram showing the structure of an ink-jet recording apparatus.

The present invention will be described in detail below.

The present invention is an alkenyl ether compound that comprises at least one of an aromatic carboxylic acid having a fluorine atom and an aromatic carboxylic acid ester having a fluorine atom, which is a polymeric compound preferably represented by the general formula, (1):

wherein X represents an alkenyl group; each A represents independently a linear or branched alkylene group of 1 to 15 carbon atoms which may be substituted; m represents an integer of 0 to 30; B represents a single bond or an alkylene group which may be substituted; each D represents independently an aromatic ring in which at least one hydrogen atom attached to the ring is replaced by a fluorine atom; n represents an integer of 1 to 10; and R represents a hydrogen atom, an alkyl group which may be substituted, or an aromatic ring which may be substituted.

Preferred examples of the alkenyl group include ethynyl, propenyl, butenyl, pentenyl and hexenyl.

It is preferably a compound represented by the following general formula (5):

In the above general formula (5), A represents a linear or branched alkylene group of 1 to 15 carbon atoms, preferably 2 to 10 carbon atoms, which may be substituted. Examples of the substituent for the alkylene group include methyl, ethyl, propyl and phenyl.

In the above general formula (5), m represents an integer of 0 to 30, preferably 1 to 10. When m is 2 or more, the respective A's may be the same or different from each other.

In the above general formula (5), B represents a single bond or an alkylene group which may be substituted. Examples of such an alkylene group include methylene, ethylene, propylene, butylenes, pentylene, hexylene, heptylene and octylene.

In the above general formula (5), D represents an aromatic ring in which at least one hydrogen atom attached to the ring is displaced by a fluorine atom. Examples of such an aromatic ring include phenyl, pyridylene, pyrimidyl, naphthyl, anthranyl, phenanthranyl, thiophenyl and furanyl. The types of substitution include monofluoro substitution, difluoro substitution, trifluoro substitution, tetrafluoro substitution, and substitution with more numbers of fluorine atoms such as 5, 6, 7 or 8 fluorine atoms. However, it is preferable that the aromatic ring is substituted with at least two fluorine atoms.

In the above general formula (5), n represents an integer of 1 to 10, preferably of 1 to 5. When n is 2 or more, the respective D's may be the same or different from each other.

In the above general formula (5), R represents a hydrogen atom, an alkyl group which may be substituted, or an aromatic ring which may be substituted. As the alkyl group, alkyl groups of 1 to 10 carbon atoms are preferable. Examples of the aromatic ring include a phenyl group, a pyridyl group and a biphenyl group. Examples of the substituent include an alkyl group and an alkoxy group.

The fluorine-substituted aromatic carboxylic acids represented by the general formula (1) have acidities different from those of the aliphatic carboxylic acids and are therefore extremely useful in their feasibility of providing various functional polymer materials with different acidities as polymer compounds having the vinyl ether repeating units. Also from the viewpoint of increasing the acidity, it is preferable that the aromatic ring is substituted with at least two fluorine atoms. Moreover, in order to control the property of each block segment related to fluorophilicity or fluorophobicity, it is preferable that the aromatic ring is substituted with as many fluorine atoms as possible.

Specific examples of the polymeric compound represented by the general formula (1) include the following compounds:

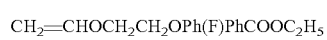

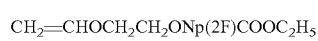

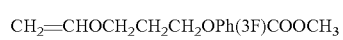

CH₂=CHO(CH₂CH₂O)₂Ph(3F)COOC₃H₇

CH₂=CHO(CH₂CH₂O)₂Ph(2F)COOCH₃

CH₂=CHO(CH₂CH₂O)₂Ph(2F)COOC₂H₅

CH₂=CHO(CH₂CH₂O)₃Ph(4F)COOC₂H₅

CH₂=CHO(CH₂CH₂O)₂Np(F)COOC₂H₅

CH₂=CHO(CH₂CH₂O)₃Np(4F)COOC₂H₅

CH₂=CHO(CH₂CH₂O)₃Np(5F)COOH

CH₂=CHOCH₂CH₂O(CH₂)₂Ph(3F)COOCH₃

CH₂=CHOCH₂CH₂O(CH₂)₃Ph(3F)COOCH₃

CH₂=CHOCH₂CH₂O(CH₂)₄PhPh(3F)COOCH₃

CH₂=CHOCH₂CH₂O(CH₂)₅Np(3F)COOCH₃

CH₂=CHO(CH₂CH₂O)₆Ph(3F)COOCH₃

CH₂=CHO(CH₂CH₂O)₇PhPh(3F)COOCH₃

CH₂=CHOCH₂CH₂O(CH₂CH₂CH₂O)₂Ph(3F)COOCH₃

CH₂=CHOCH₂CH₂OPyPh(2F)COOCH₃

CH₂=CHOCH₂CH₂OPyPh(2F)COOC₂H₅

CH₂=CHOCH₂CH₂O(CH₂)₂₀Ph(2F)COOCH₃

CH₂=CHO(CH₂CH₂O)₂(CH₂)₂Ph(2F)COOC₂H₅

CH₂=CHO(CH₂CH₂O)₃(CH₂)₃Ph(2F)COOC₂H₅

CH₂=CHO(CH₂CH₂O)₁₀Ph(2F)COOC₂H₅

CH₂=CHO(CH₂CH₂O)₂₀Ph(2F)COOC₂H₅

CH₂=CHO(CH₂CH₂O)₂(CH₂)₆OPh(2F)COOC₂H₅

CH₂=CHO(CH₂CH₂O)₅(CH₂)₇OPh(3F)COOC₂H₅

CH₂=CHO(CH₂CH₂O)₆(CH₂)₈OPh(3F)COOC₂H₅

CH₂=CHO(CH₂CH₂O)₁₀(CH₂)₁₀OPh(3F)COOC₂H₅

CH₂=CHO(CH₂CH₂O)₁₅(CH₂)₁₅OPh(3F)COOC₂H₅

CH₂=CHO(CH₂CH₂O)₂(CH₂)₂₀OPh(3F)COOC₂H₅

CH₂=CHOCH₂CH₂CH₂CH₂CH₂CH₂O(CH₂)₂OPh(3F)COOC₂H₅

CH₂=CHOCH₂CH₂CH₂CH₂O(CH₂)₃OPh(3F)COOC₂H₅

CH₂=CHOCH₂CH₂CH₂CH₂O(CH₂)₄OPh(3F)COOC₂H₅

CH₂=CHOCH₂CH₂CH₂CH₂CH₂CH₂CH₂O(CH₂)₅OPh(3F)COOC₂H₅

CH₂=CHOCH₂CH₂CH₂CH₂CH₂CH₂O(CH₂)₆OPh(3F)COOC₂H₅

CH₂=CHOCH(CH₃)CH₂O(CH₂)₇OPh(3F)COOC₂H₅

CH₂=CHOCH(CH₃)CH₂O(CH₂)₈OPh(3F)COOC₂H₅

CH₂=CHOCH₂CH(CH₃)O(CH₂)₁₀OPh(3F)COOC₂H₅

CH₂=CHOCH(C₂H₅)CH₂O(CH₂)₁₅OPh(4F)COOC₂H₅

CH₂=CHOCH₂CH(CH₃)O(CH₂)₂₀OPh(2F)COOC₂H₅

CH₂=CHOCH₂CH₂O(CH₂)₂OPh(3F)COOPhH

CH₂=CHOCH₂CH₂O(CH₂)₃OPh(3F)COOCH₂PhH

CH₂=CHOCH₂CH₂O(CH₂)₄OPh(4F)COOPyrH

CH₂=CHOCH₂CH₂CH₂CH₂O(CH₂)₅OPyr(3F)COOPhH

CH₂=CHOCH₂CH₂O(CH₂)₆OPh(3F)COOPh(OCH₃)

CH₂=CHO(CH₂CH₂O)₂(CH₂)₇OPh(F)COOPh(OCH₃)

CH₂=CHOCH₂CH₂O(CH₂)₈OPh(4F)COOPh(OCH₃)

CH₂=CHOCH₂CH₂O(CH₂)₁₀OPh(3F)COOPh(OCH₃)

CH₂=CHOCH₂CH₂O(CH₂)₁₅OPh(2F)COOPh(OCH₃)

CH₂=CHOCH₂CH₂O(CH₂)₂₀OPh(3F)COOPh(OCH₃)

In the above examples, Ph represents 1,4-phenylene or 1,3-phenylene, Py represents 2,5-pyrimidylene, and Pyr represents 2,5-pyridylene. Np represents 2,6-naphthylene, 1,4-naphthylene or 1,5-naphthylene. The expression Ph (F) represents 2- or 3-monofluoro substitution. The expression Ph (2F) represents 2,3-, 2,6-, 2,5- or 3,5-difluoro substitution. The expression Ph(3F) represents 2,3,5- or 2,3,6-trifluoro substitution. The expression Ph(4F) represents 2,3,5,6-tetrafluoro substitution. In the case of other aromatic ring structures also, the arabic numeral in parentheses represents the number of fluorine atoms for substitution and indicates that the substitution is effected at any positions.

As an example of the synthesizing method of the polymeric compound represented by the general formula (1), there may be included an etherification method shown by the following reaction formula (1):

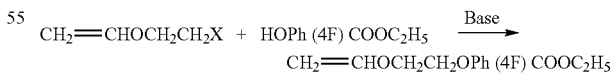

Reaction Formula (1)

$$CH_2=CHOCH_2CH_2X + HOPh(4F)COOC_2H_5 \xrightarrow{Base} CH_2=CHOCH_2CH_2OPh(4F)COOC_2H_5$$

wherein X represents a halogen atom.

Moreover, the present invention is a polymer compound comprising a polyalkenyl ether repeating unit comprising at least one selected from a carboxylic acid, a carboxylic acid ester and a carboxylic acid salt, each having a fluorine atom in a side chain thereof, which preferably has a repeating unit represented by the general formula (2):

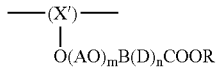
(2)

wherein X' represents a polyalkenyl group; each A represents independently a linear or branched alkylene group of 1 to 15 carbon atoms which may be substituted; m represents an integer of 0 to 30; B represents a single bond or an alkylene group which may be substituted; each D represents independently an aromatic ring in which at least one hydrogen atom attached to the ring is displaced by a fluorine atom; n represents an integer of 1 to 10; and R represents a hydrogen atom, an alkyl group which may be substituted.

The repeating unit structure represented by the general formula (2) is preferably a unit structure represented by the following general formula (6):

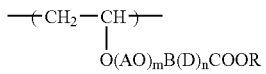
(6)

wherein each A represents independently a linear or branched alkylene group of 1 to 15 carbon atoms which may be substituted; m represents an integer of 0 to 30; B represents a single bond or an alkylene group which may be substituted; each D represents independently an aromatic ring in which at least one hydrogen atom attached to the ring is displaced by a fluorine atom; n represents an integer of 1 to 10; and R represents a hydrogen atom, an alkyl group which may be substituted, or an aromatic ring structure which may be substituted.

Incidentally, it is to be noted that preferred ranges and specific examples of A, m, B, D, n and R are the same as those described for the above general formula (1).

The general formula (6) in accordance with the present invention is characterized by having the fluorine-substituted aromatic carboxylic acid derivative at a terminal thereof. The fluorine-substituted aromatic carboxylic acids have acidities different from those of the aliphatic carboxylic acids and are therefore extremely useful in their feasibility of providing various functional polymer materials with different acidities as polymer compounds having the vinyl ether repeating units. Also from the viewpoint of increasing the acidity, it is preferable that the aromatic ring is substituted with at least two fluorine atoms. Moreover, in order to control the property of each block segment related to fluorophilicity or fluorophobicity, it is preferable that the aromatic ring is substituted with as many fluorine atoms as possible.

Specific examples of the repeating unit structure represented by the general formula (2) include the following unit structures:

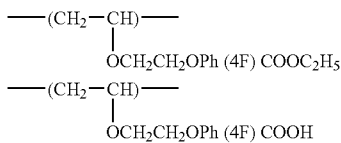

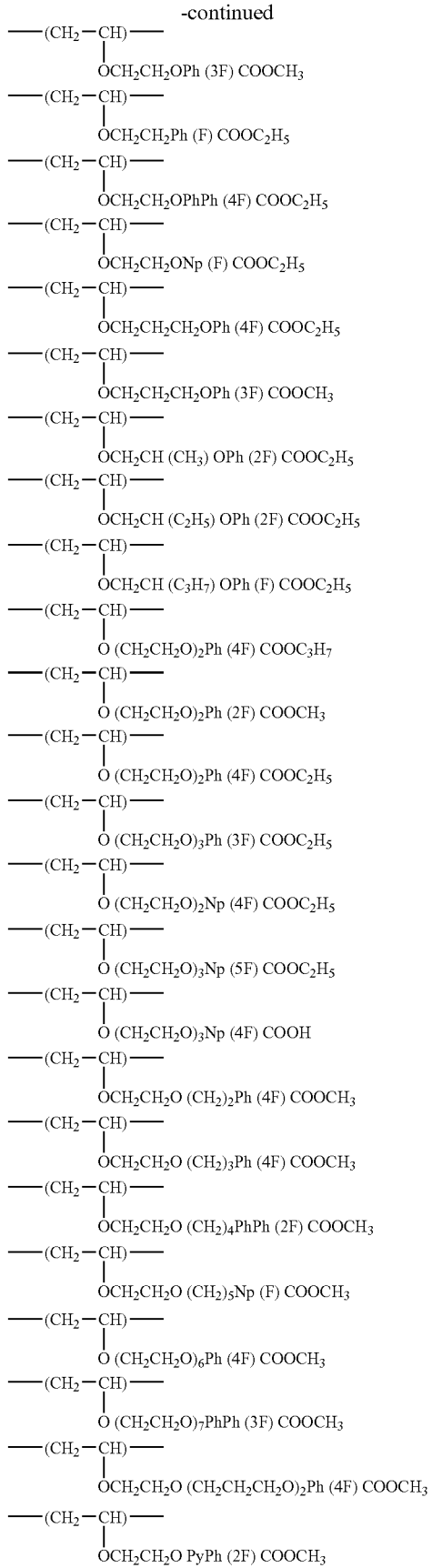

-continued

—(CH$_2$—CH)—
　　　|
　　OCH$_2$CH$_2$O PyPh (3F) COOC$_2$H$_5$

—(CH$_2$—CH)—
　　　|
　　OCH$_2$CH$_2$O (CH$_2$)$_{20}$Ph (2F) COOCH$_3$

—(CH$_2$—CH)—
　　　|
　　O(CH$_2$CH$_2$O)$_2$ (CH$_2$)$_2$Ph (3F) COOC$_2$H$_5$

—(CH$_2$—CH)—
　　　|
　　O(CH$_2$CH$_2$O)$_3$ (CH$_2$)$_3$Ph (2F) COOC$_2$H$_5$

—(CH$_2$—CH)—
　　　|
　　O(CH$_2$CH$_2$O)$_{10}$Ph (4F) COOC$_2$H$_5$

—(CH$_2$—CH)—
　　　|
　　O(CH$_2$CH$_2$O)$_{20}$Ph (3F) COOC$_2$H$_5$

—(CH$_2$—CH)—
　　　|
　　O(CH$_2$CH$_2$O)$_2$ (CH$_2$)$_6$OPh (2F) COOC$_2$H$_5$

—(CH$_2$—CH)—
　　　|
　　O(CH$_2$CH$_2$O)$_5$ (CH$_2$)$_7$OPh (3F) COOC$_2$H$_5$

—(CH$_2$—CH)—
　　　|
　　O(CH$_2$CH$_2$O)$_6$ (CH$_2$)$_8$OPh (2F) COOC$_2$H$_5$

—(CH$_2$—CH)—
　　　|
　　O(CH$_2$CH$_2$O)$_{10}$ (CH$_2$)$_{10}$OPh (2F) COOC$_2$H$_5$

—(CH$_2$—CH)—
　　　|
　　O(CH$_2$CH$_2$O)$_{15}$ (CH$_2$)$_{15}$OPh (3F) COOC$_2$H$_5$

—(CH$_2$—CH)—
　　　|
　　O(CH$_2$CH$_2$O)$_2$ (CH$_2$)$_{20}$OPh (2F) COOC$_2$H$_5$

—(CH$_2$—CH)—
　　　/
　　OCH$_2$CH$_2$CH$_2$CH$_2$CH$_2$CH$_2$CH$_2$CH$_2$O(CH$_2$)$_2$OPh(3F)COOC$_2$H$_5$

—(CH$_2$—CH)—
　　　|
　　OCH$_2$CH$_2$CH$_2$CH$_2$O (CH$_2$)$_3$OPh (2F) COOC$_2$H$_5$

—(CH$_2$—CH)—
　　　|
　　OCH$_2$CH$_2$CH$_2$CH$_2$O (CH$_2$)$_4$OPh (2F) COOC$_2$H$_5$

—(CH$_2$—CH)—
　　　/
　　OCH$_2$CH$_2$CH$_2$CH$_2$CH$_2$CH$_2$CH$_2$CH$_2$O(CH$_2$)$_5$OPh(4F)COOC$_2$H$_5$

—(CH$_2$—CH)—
　　　|
　　OCH$_2$CH$_2$CH$_2$CH$_2$CH$_2$CH$_2$O(CH$_2$)$_6$OPh(F)COOC$_2$H$_5$

—(CH$_2$—CH)—
　　　|
　　OCH (CH$_3$) CH$_2$O (CH$_2$)$_7$OPh (2F) COOC$_2$H$_5$

—(CH$_2$—CH)—
　　　|
　　OCH (CH$_3$) CH$_2$O (CH$_2$)$_8$OPh (3F) COOC$_2$H$_5$

—(CH$_2$—CH)—
　　　|
　　OCH$_2$CH (CH$_3$) O (CH$_2$)$_{10}$OPh (4F) COOC$_2$H$_5$

—(CH$_2$—CH)—
　　　|
　　OCH (C$_2$H$_5$) CH$_2$O (CH$_2$)$_{15}$OPh (2F) COOC$_2$H$_5$

—(CH$_2$—CH)—
　　　|
　　OCH$_2$CH (CH$_3$) O (CH$_2$)$_{20}$OPh (F) COOC$_2$H$_5$

—(CH$_2$—CH)—
　　　|
　　OCH$_2$CH$_2$O (CH$_2$)$_2$OPh (4F) COOPhH

—(CH$_2$—CH)—
　　　|
　　OCH$_2$CH$_2$O (CH$_2$)$_3$OPh (3F) COOCH$_2$PhH

-continued

—(CH$_2$—CH)—
　　　|
　　OCH$_2$CH$_2$O (CH$_2$)$_4$OPh (4F) COOPyrH

—(CH$_2$—CH)—
　　　|
　　OCH$_2$CH$_2$CH$_2$CH$_2$O (CH$_2$)$_5$OPyr (F) COOPhH

—(CH$_2$—CH)—
　　　|
　　OCH$_2$CH$_2$O (CH$_2$)$_6$OPh (4F) COOPh (OCH$_3$)

—(CH$_2$—CH)—
　　　|
　　O (CH$_2$CH$_2$O)$_2$ (CH$_2$)$_7$OPh (4F) COOPh (OCH$_3$)

—(CH$_2$—CH)—
　　　|
　　OCH$_2$CH$_2$O (CH$_2$)$_8$OPh (2F) COOPh (OCH$_3$)

—(CH$_2$—CH)—
　　　|
　　OCH$_2$CH$_2$O (CH$_2$)$_{10}$OPh (3F) COOPh (OCH$_3$)

—(CH$_2$—CH)—
　　　|
　　OCH$_2$CH$_2$O (CH$_2$)$_{15}$OPh (2F) COOPh (OCH$_3$)

—(CH$_2$—CH)—
　　　|
　　OCH$_2$CH$_2$O (CH$_2$)$_{20}$OPh (4F) COOPh (OCH$_3$)

In the above examples, Ph represents 1,4-phenylene or 1,3-phenylene, Py represents 2,5-pyrimidylene, and Pyr represents 2,5-pyridylene. Np represents 2,6-naphthylene, 1,4-naphthylene or 1,5-naphthylene. The expression Ph(F) represents 2- or 3-monofluoro substitution. The expression Ph(2F) represents 2,3-, 2,6-, 2,5- or 3,5-difluoro substitution. The expression Ph(3F) represents 2,3,5- or 2,3,6-trifluoro substitution. The expression Ph(4F) represents 2,3,5,6-tetrafluoro substitution. In the case of other aromatic ring structures also, the arabic numeral in parentheses represents the number of fluorine atoms for substitution and indicates that the substitution is effected at any positions.

The polymer compound having the repeating unit structure represented by the above general formula (2) can preferably be obtained by polymerizing the polymeric compound represented by the above general formula (1). The polymerization herein is mainly a cationic polymerization. Examples of an initiator used herein include a protonic acid such as hydrochloric acid, sulfuric acid, methanesulfonic acid, trifluoroacetic acid, trifluoromethanesulfonic acid or perchloric acid, or a combination of a Lewis acid such as BF$_3$, AlCl$_3$, TiCl$_4$, SnCl$_4$, FeCl$_3$, RAlCl$_2$ or R$_{1.5}$AlCl$_{1.5}$ (wherein R represents alkyl) with a cation source (wherein examples of such a cation source include a protonic acid, and an adduct obtained from water, alcohol, vinyl ether and a carboxylic acid). By making such an initiator coexist with the polymeric compound (monomer) represented by the general formula (1), a polymerization reaction will proceed to synthesize the polymer compound.

The number-average molecular weight of the polymer of the present invention having the repeating unit structure represented by the general formula (2) is generally not less than 200 but no more than 10,000,000, and preferably not less than 1,000 but no more than 1,000,000. If the number-average molecular weight exceeds 10,000,000, it causes too much entanglement or twisting in a polymer chain or between polymer chains, and it might become difficult for the polymer to be dispersed in a solvent. In contrast, if the number-average molecular weight is less than 200, the molecular weight is so small that a steric effect as a polymer might be hardly obtained. The polymer of the present invention may be either a homopolymer consisting of a single kind repeating unit structure, or copolymer consisting of multiple kinds of repeating unit structures. The repeating unit structure represented by the general formula (2) may be contained in the polymer preferably in an amount of 10 mol % or more. In addition, the content of the polyalkenyl ether repeating unit structure may also be preferably 50 mol % or more, and more preferably 80 mol % or more.

Moreover, the polymer of the present invention is a polymer having a repeating unit structure represented by the following general formula (3):

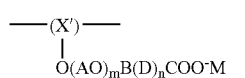
(3)

wherein X' represents a polyalkenyl group; each A represents independently a linear or branched alkylene group of 1 to 15 carbon atoms which may be substituted; m represents an integer of 0 to 30; B represents a single bond or an alkylene group which may be substituted; each D represents independently an aromatic ring in which at least one hydrogen atom attached to the ring is displaced by a fluorine atom; n represents an integer of 1 to 10; and M represents a monovalent or polyvalent metal cation.

Preferred examples of the polyalkenyl include polyethynyl, polypropenyl, polybutenyl, polypentenyl and polyhexenyl.

The repeating unit structure represented by the general formula (3) is preferably a unit structure represented by the following general formula (7):

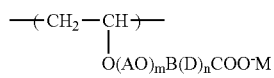
(7)

wherein each A represents independently a linear or branched alkylene group of 1 to 15 carbon atoms which may be substituted; m represents an integer of 0 to 30; B represents a single bond or an alkylene group which may be substituted; each D represents independently an aromatic ring in which at least one hydrogen atom attached to the ring is displaced by a fluorine atom; n represents an integer of 1 to 10; and M represents a monovalent or polyvalent metal cation.

It is to be noted that preferred ranges and specific examples of A, m, B, D and n are the same as those described for the above general formula (1).

In the above general formula (7), M represents a monovalent or polyvalent metal cation. Specific examples of M as a monovalent metal cation include sodium, potassium and lithium. Specific examples of M as a polyvalent metal cation include magnesium, calcium, nickel and iron. When M represents a polyvalent metal cation, M forms counterions for two or more COO⁻ groups as anions.

The polymer of the present invention having the repeating unit structure represented by the general formula (3) can be obtained by subjecting to alkaline hydrolysis or alkaline neutralization, a terminal ester portion of a corresponding polymer having the repeating unit structure represented by the above general formula (2). It is also possible to obtain the above polymer of the present invention by hydrolysis with an acid followed by alkaline treatment. However, the former method is preferable.

Specific examples of the repeating unit structure represented by the general formula (3) include the following unit strictures:

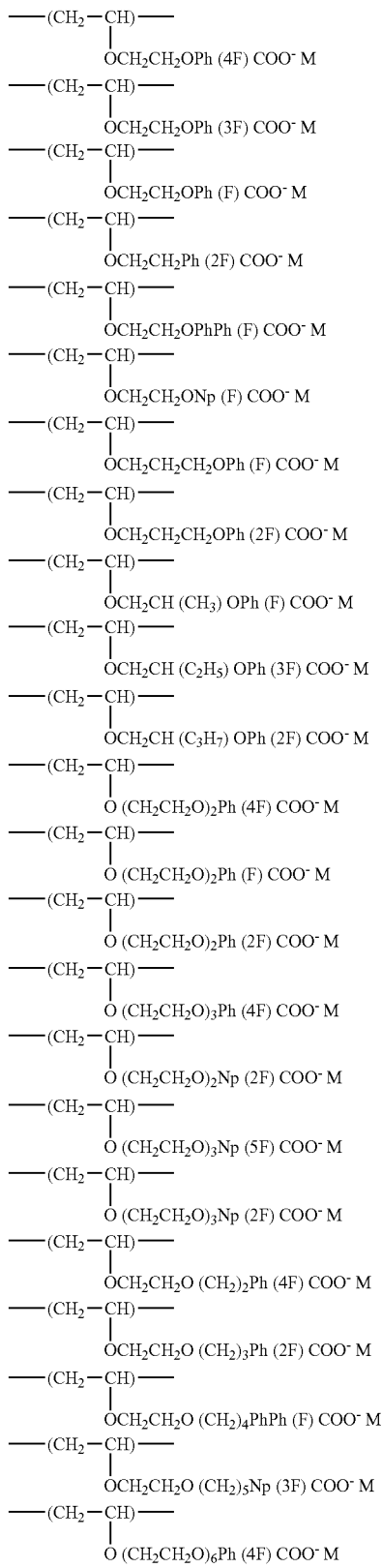

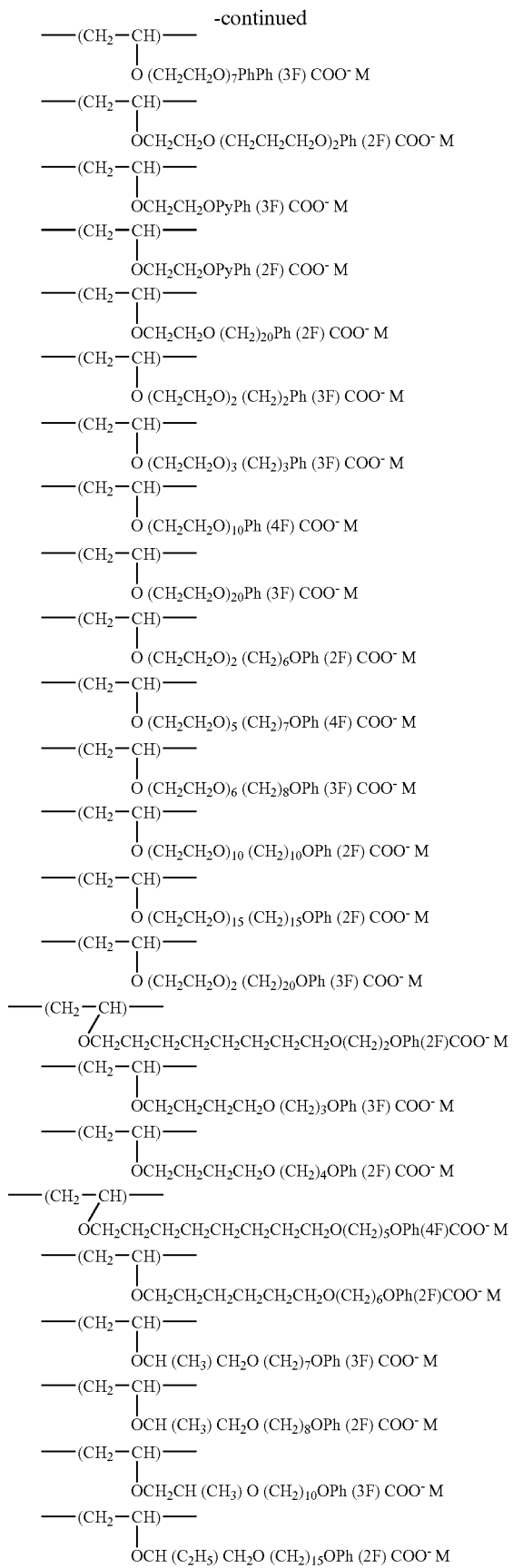
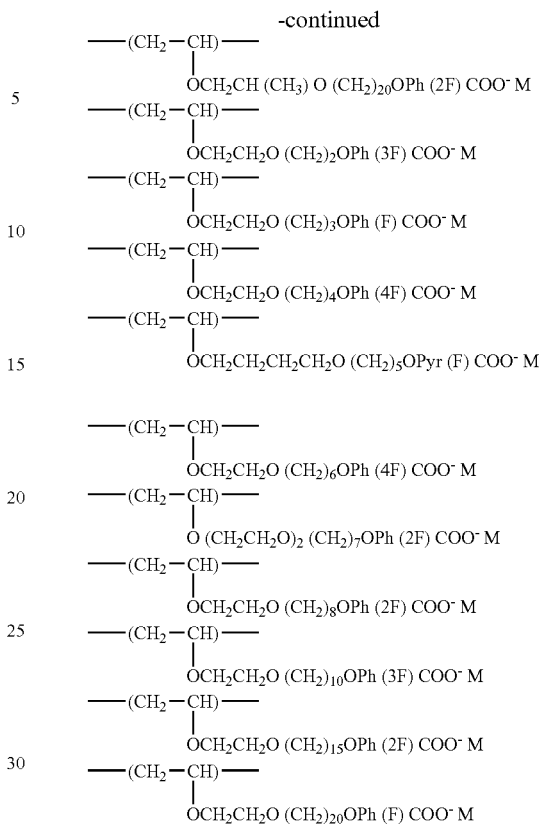

In the above examples, Ph represents 1,4-phenylene or 1,3-phenylene, Py represents 2,5-pyrimidylene, and Pyr represents 2,5-pyridylene. Np represents 2,6-naphthylene, 1,4-naphthylene or 1,5-naphthylene. The expression Ph(F) represents 2- or 3-monofluoro substitution. The expression Ph(2F) represents 2,3-, 2,6-, 2,5- or 3,5-difluoro substitution. The expression Ph(3F) represents 2,3,5- or 2,3,6-trifluoro substitution. The expression Ph(4F) represents 2,3,5,6-tetrafluoro substitution. In the case of other aromatic ring structures also, the arabic numeral in parentheses represents the number of fluorine atoms for substitution and indicates substitution is effected at any positions.

The number-average molecular weight of the polymer of the present invention having the repeating unit structure represented by the general formula (3) is generally not less than 200 but no more than 10,000,000, and preferably not less than 1,000 but no more than 1,000,000. If the number-average molecular weight is more than 10,000,000, it causes too much entanglement or twisting in a polymer chain or between, polymer chains, and it might become difficult for the polymer to be dispersed in a solvent. In contrast, if the number-average molecular weight is less than 200, the molecular weight is so small that a steric effect as a polymer might be hardly obtained. The polymer of the present invention may be either a homopolymer consisting of a single kind repeating unit structure, or copolymer consisting of multiple kinds of repeating unit structures. The repeating unit structure represented by the general formula (3) may be contained in the polymer preferably in an amount of 10 mol % or more. In addition, the content of the polyalkenyl ether repeating unit structure may also be preferably 50 mol % or more, and more preferably 80 mol % or more.

Next, the fourth aspect of the present invention is a block polymer, which comprises a polyalkenyl ether repeating unit comprising an aromatic structure having a fluorine atom in a side chain thereof in at least one block segment. The term block polymer is used to mean a copolymer obtained by binding at least two different types of polymer segment structures by covalent bonding, and such a block polymer is also called a block copolymer. Moreover, the block polymer of the present invention is preferably a block polymer comprising a polyalkenyl ether repeating unit comprising at least one selected from a carboxylic acid, a carboxylic acid ester and a carboxylic acid salt, each having a fluorine atom in a side chain thereof in at least one block segment. Furthermore, when the above structure is a fluorine-substituted aromatic carboxylic acid structure, the pKa of the carboxylic acid is preferably 2.5 or less. The fact that the pKa is 2.5 or less means that the compound can sufficiently be in a dissociative state up to a pH close to 3, which shows extremely stable ionicity and hydrophilicity. It is to be noted that pKa is an acid dissociation index and represents the logarithmic value of the reciprocal of an acid dissociation constant Ka. When the concentration of a certain acid (HA) that is not dissociated in a solution is defined as [HA], and when the concentration of a dissociated acid $H^+$ and the concentration of its counterion are defined as $[H^+]$ and $[A^-]$, respectively, the acid dissociation constant Ka is expressed as $Ka=[H^+][A^-]/[HA]$. Accordingly, pKa is obtained by the following expression: $pKa=-\log[H^+]-\log([A^-]/[HA])=pH-\log([A^-]/[HA])$. Incidentally, in the present invention, pKa is obtained, while a polymer is not defined as a unit of the number of moles, but one carboxylic acid repeating unit is defined as a unit of the number of moles.

The block polymer of the present invention is preferably a block polymer having in at least one block segment thereof, a repeating unit structure represented by the following general formula (4):

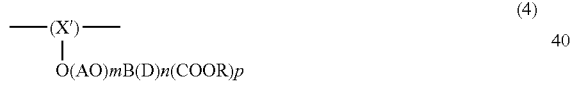

wherein X' represents a polyalkenyl group; each A represents independently a linear or branched alkylene group of 1 to 15 carbon atoms which may be substituted; m represents an integer of 0 to 30; B represents a single bond or an alkylene group which may be substituted; each D represents independently an aromatic ring in which at least one hydrogen atom attached to the ring is displaced by a fluorine atom; n represents an integer of 1 to 10; p represents 0 or 1; and COOR represents a carboxylic acid ester, a carboxylic acid, or a salt of a carboxylic acid anion and a cation.

Specific examples of the repeating unit structure represented by the general formula (4) include the above listed examples of the repeating unit structures represented by the general formulas (2) and (3). In addition, specific examples further include those in which the carboxylic acid moieties of the above listed structures are substituted with hydrogen or fluorine atoms.

The block polymer of the present invention does not only have a block segment containing the repeating unit structure represented by the above general formula (4), but also have a block segment containing at least another repeating unit structure. More specifically, a block segment containing a repeating unit represented by the following general formula (8) is preferably used:

wherein:

$R^1$ is selected from the group consisting of a linear, branched or cyclic alkyl group of 1 to 18 carbon atoms, -Ph, -Pyr, -Ph-Ph, -Ph-Pyr, $—(CH(R^5)—CH(R^6)—O)_p—R^7$ and $—(CH_2)_m—(O)_n—R^7$, and hydrogen atom(s) in the aromatic ring may be replaced by linear or branched alkyl group(s) of 1 to 4 carbon atoms, and carbon atom(s) in the aromatic ring may be replaced by nitrogen atom(s);

p represents an integer of 1 to 18;

m represents an integer of 1 to 36;

n represents 0 or 1;

each of $R^5$ and $R^6$ represents independently a hydrogen atom or $—CH_3$;

$R^7$ is selected from the group consisting of a hydrogen atom, a linear, branched or cyclic alkyl group of 1 to 18 carbon atoms, -Ph, -Pyr, -Ph-Ph, -Ph-Pyr, —CHO, $—CH_2CHO$, $—CO—CH=CH_2$, $—CO—C(CH_3)=CH_2$ and $—CH_2COOR_8$, and when $R^7$ is other than a hydrogen atom, hydrogen atom(s) attached to carbon atom(s) in $R^7$ may be replaced by a linear or branched alkyl group of 1 to 4 carbon atoms, —F, —Cl or —Br, and carbon atom(s) in the aromatic ring may be replaced by nitrogen atom(s);

$R^8$ represents a hydrogen atom or an alkyl group of 1 to 5 carbon atoms;

Ph represents a phenyl or phenylene group; and

Pyr represents a pyridyl group.

Specific examples of the $R^1$ structure represented by the general formula (8) are as follows:

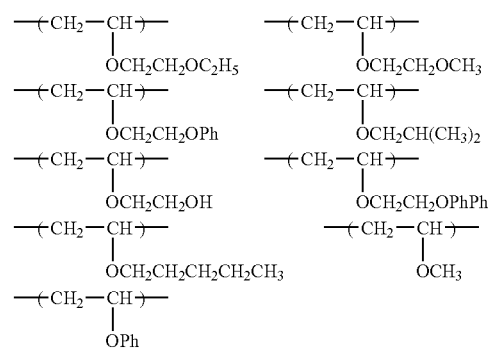

In the above examples, Ph represents a phenyl or phenylene group.

Moreover, each block segment of the block polymer of the present invention may consist of a single kind repeating unit, or may consist of multiple kinds of repeating unit structures. Examples of a block segment consisting of multiple kinds of repeating units include a random copolymer and a graduation copolymer whose compositional ratio is gradually changed. Furthermore, the block polymer of the present invention is a block polymer having two or more block segments and may also be a graft polymer obtained by graft binding of the above block polymer to other polymers.

In the present invention, the content of the repeating unit structure represented by the general formula (4) is preferably within the range of 0.01 to 99 mol %, more preferably within the range of 1 to 90 mol % on the basis of the whole block polymer. When the above content is within the range of 0.01 and 99 mol %, carboxylic acid moieties can interact so well with each other that they may function sufficiently, which is preferable. Furthermore, the content of the repeating unit structure on the basis of the block segment is generally 5 mol % or more, preferably 20 mol % or more, more preferably 50 mol % or more, and furthermore preferably 80% or more, and the content may also be 100 mol %. The ratio of the polyalkenyl ether repeating unit structure in the block polymer of the present invention is preferably 50 mol % or more, and more preferably 80 mol %, and may also be 100 mol % in the block polymer except for both terminal portions.

The number-average molecular weight (Mn) of the block polymer of the present invention is not less than 200 but no more than 10,000,000, and the range preferably used is not less than 1,000 but no more than 1,000,000. When the number-average molecular weight is not less than 200 but no more than 10,000,000, it causes less entanglement or twisting in a polymer chain or between polymer chains, so that the polymer is easily dispersed in a solvent and can sufficiently exhibit the steric effect as a polymer.

The polymerization degree of each block segment is preferably not less than 3 but no more than 10,000, more preferably not less than 5 but no more than 5,000, and most preferably not less than 10 but no more than 4,000.

Further, in order to improve the dispersion stability and the inclusion property (encapsulation property), it is preferable that the molecular motion of the block polymer is more flexible. This is because when the molecular motion of the block polymer is flexible, the block polymer easily becomes entangled (or intertwined) physically with the surface of a functional substance to have a high affinity therewith, and also because a coating layer is easily formed on a recording medium. On this account, the glass transition temperature Tg of the main chain of the block polymer is preferably 20° C. or less, more preferably 0° C. or less, and further more preferably −20° C. or less. In this respect also, the polymer having a polyvinyl ether structure is preferably used because it generally has a low glass transition temperature and flexible characteristics. In the above described examples of the repeating unit structures, their glass transition temperature is approximately −20° C. or less in most cases.

In a preferred embodiment, the block polymer of the present invention is an amphiphilic polymer. Because of its amphiphilicity, the block polymer easily takes a micellar structure, whereby it includes functional substances in the core portion of the micelle or adsorbs the substances to the hydrophobic portion thereof, so that the functional substances can be well dispersed in the block polymer. When at least one block segment is solvophobic and at least one block segment is solvophilic in the block polymer of the present invention, amphiphilicity develops. As a solvent with regard to which the solvophobicity and solvophilicity are exhibited, an aqueous solvent is preferably used. In other words, the block polymer of the present invention preferably has at least one hydrophobic segment and at least one hydrophilic segment. For example, the hydrophobic segment is a structure represented by the general formula (8) wherein $R^1$ is an alkyl group or phenyl group, and the hydrophilic segment is a structure represented by the general formula (3). Moreover, with the block polymer of the present invention, it is also possible to form an amphiphilic structure that is based on properties of fluorophilicity and fluorophobicity, as well as being based on the amphiphilicity in terms of hydrophilicity and hydrophobicity. It is possible to form in an organic solvent such a micellar structure that fluorophilic segments form a core and fluorophobic and organic-solvent-philic segments are located outside thereof. The repeating unit structure represented by the general formula (4) is used as a main repeating unit structure in the fluorophilic segment.

Polymerization of the block polymer of the present invention is mainly a cationic polymerization. Examples of an initiator used herein include a protonic acid such as hydrochloric acid, sulfuric acid, methanesulfonic acid, trifluoroacetic acid, trifluoromethanesulfonic acid or perchloric acid, or a combination of a Lewis acid such as $BF_3$, $AlCl_3$, $TiCl_4$, $SnCl_4$, $FeCl_3$, $RAlCl_2$ or $R_{1.5}AlCl_{1.5}$ (wherein R represents alkyl), with a cation source (wherein examples of such a cation source include a protonic acid, and an adduct obtained from water, alcohol, vinyl ether and a carboxylic acid). By making such an initiator coexist with the polymeric compound (monomer), a polymerization reaction will proceed to synthesize the block polymer.

A polymerization method that is more preferably used in the present invention will be explained below. There have been many reports on methods of synthesizing a polymer containing a polyvinyl ether structure. Among others, the cationic living polymerization method according to Aoshima et al. is representative (Polymer Bulletin Vol. 15, 1986, p.417; and Japanese Patent Application Laid-Open Nos. H11-322942 and H11-322866). By synthesizing a polymer by the cationic living polymerization, various polymers such as a homopolymer, copolymer consisting of two or more component monomers, as well as block polymer, graft polymer, graduation polymer, and the like can be synthesized while making their lengths (molecular weights) equal. Moreover, the living polymerization can also be carried out with an $HI/I_2$ system or $HCl/SnCl_4$ system.

The fifth feature of the present invention will be described. The fifth feature of the present invention relates to a block polymer having at least three block segments, two segments of which are solvophobic and solvophilic, and another segment of which has a repeating unit structure having a fluorine-substituted aromatic structure therein. The above block segment of the block polymer of the present invention, which has a repeating unit structure having a fluorine-substituted aromatic structure, preferably has solvophilicity or fluorophilicity. The term "fluorophilicity" has a meaning extremely close to the meaning that other segments have fluorophobicity. Namely, this is similar to the fact that as for the hydrophobicity, the hydrophobic interaction is exhibited, not based on affinity between hydrophobic groups, but as a result of exclusion from the affinity between hydrophilic groups. Thus, the term "fluorophilicity" will be herein employed although not based on affinity between fluorophilic groups. When a block segment having a repeating unit structure having a fluorine-substituted aromatic structure is fluorophilic, it means that the block polymer has segments with three different properties such as solvophilicity, solvophobicity and fluorophilicity. Accordingly, it becomes possible for the block polymer to form a specific microphase separated structure, to form a specific micellar structure, or to include a fluorophilic functional substance, which, in general, is difficult to disperse. The same holds good of the polymer compound of the fourth feature of the present invention.

Moreover, in a block polymer as another preferred example of the fifth feature of the present invention, wherein a block segment having a repeating unit structure with a fluorine-substituted aromatic structure is solvophilic, it is particularly preferable that the repeating unit structure with a fluorine-substituted aromatic structure has at least one selected from a carboxylic acid, a carboxylic acid ester and a carboxylic acid salt therein. Thereby, the dissociative property of the carboxylic acid is extremely enhanced, so as to secure the high dispersion stability in an aqueous solvent that is preferably used.

As with the above-described features of the present invention, the above block polymer of the fifth feature of the present invention preferably comprises a polyalkenyl ether repeating unit structure, and more preferably consists of polyalkenyl ether repeating unit structures. In the present invention, specific examples of block polymers comprising a polyalkenyl ether unit structure are included. With the sixth feature of the present invention, there is provided a block polymer having at least three or more block segments, two segments of which are solvophobic and solvophilic, and another segment of which has a repeating unit structure having a fluorine-substituted aromatic structure therein. Thereby, the polymer, and a polymer composition and a recording material using the polymer exhibit extremely good characteristics. For example, in the case of using a block polymer in accordance with a particularly preferred embodiment, whose block segment having a repeating unit structure having a fluorine-substituted aromatic structure is solvophilic, extremely excellent weather resistance and fixability can be realized, as described below. It is, of course, preferable to exhibit these characteristics. However, the present invention is not particularly limited to the presence of a polyalkenyl ether main chain and is characterized by a block polymer having at least three block segments, in which two block segments are solvophobic and solvophilic and another block segment has a repeating unit structure with a fluorine-substituted aromatic structure therein. Accordingly, examples of the polymer main chain structure further include acryl, methacryl, styryl and maleyl.

The polyalkenyl ether repeating unit structure represented by the general formula (4) is a specific example of the repeating unit structure having a fluorine-substituted aromatic structure, which is preferably used. Specific examples of such a repeating unit structure are also the same as those listed above.

Moreover, a specific example of a repeating unit structure used for block segments other than the above mentioned is a compound containing a repeating unit represented by the following general formula (9):

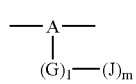
(9)

wherein A represents a polyalkenyl group which may be substituted; G represents any structure selected from —O—, —OCO—, —COO— and —CONR$^1$—; R$^1$ represents a hydrogen atom or a linear or branched alkyl group of 1 to 3 carbon atoms which may be substituted; l represents an integer of 0 or 1; each J represents independently a linear or branched alkyl or alkenyl group of 1 to 15 carbon atoms which may be substituted, in which methylene group(s) in the alkyl or alkenyl group may be displaced by oxygen atom(s) or aromatic ring(s), and hydrogen atom(s) attached to carbon atom(s) in the alkyl or alkenyl group may be displaced by hydroxyl group(s); and m represents an integer of 0 to 30.

Specific examples of the repeating unit structure represented by the general formula (9) are as follows:

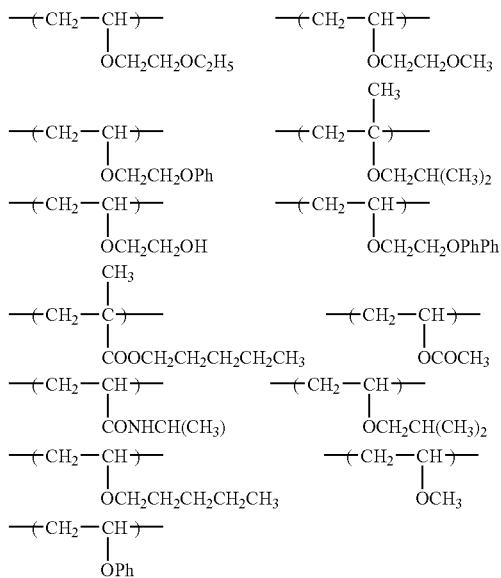

In the above examples, Ph represents a phenylene or phenyl group.

Moreover, the block polymer of the present invention can also comprise a segment that causes a phase change from hydrophilic to hydrophobic or from hydrophobic to hydrophilic in response to stimulation such as a change in temperature, exposure to electromagnetic waves, a change in pH, or a change in concentration, which is preferable. The block polymer compound of the present invention is a block polymer having at least three block segments. The block polymer compound has at least one selected from a carboxylic acid, a carboxylic acid ester and a carboxylic acid salt, and at least one fluorine atom, in a side chain of at least one segment of the block polymer, and one of the block segments may be a stimulus responsive block segment. The stimulation is preferably a change in temperature, exposure to electromagnetic waves, a change in pH, or a change in concentration, and these stimulations may also be used in combination. An ABC triblock polymer described below is a specific example of the block polymer of the present invention having stimulus responsibility, to which the present invention is, however, not limited. The ABC triblock polymer comprises the following block segment A exhibiting hydrophobicity,

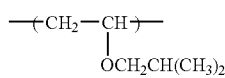

as an example of the most solvophobic repeating unit, the following block segment C having a carboxylic acid group and exhibiting hydrophilicity,

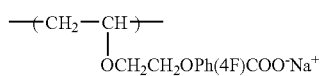

as an example of the most solvophilic repeating unit having an ionic functional group and fluorine atoms, and the following nonionic hydrophilic block segment B that is responsive to stimulation by temperature and has a smaller hydrophilicity than the hydrophilicity of the above segment C,

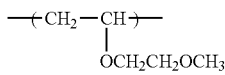

as an example of the other repeating unit. Incidentally, the above hydrophilic segment B is a block segment that is responsive to stimulation by temperature and is known to causes a phase change such that it is hydrophobic at a temperature of about 70° C. or more and becomes hydrophilic at a temperature less than that temperature, which has also been confirmed by differential scanning calorimetry (DSC).

As with the fourth feature of the present invention, in the fifth feature of the present invention, an amphiphilic block having an alkenyl ether structure as a repeating unit is used which has at least one selected from an aromatic structure, an aromatic carboxylic acid, an aromatic carboxylic acid ester and an aromatic carboxylic acid salt each having hydrogen atom(s) displaced by fluorine atom(s), in a side chain of at least one block segment. Accordingly, a higher order elaborated structure can be formed. In addition, by imparting similar properties to multiple block segments, it makes also possible to stabilize the properties. For example, when a dispersion liquid is prepared using the above-described amphiphilic block polymer and using a coloring material and water as a solvent, it is possible to include the coloring material in a micelle formed by the block polymer. Thus, a coloring material-included ink composition can easily be formed. Moreover, the particle diameters of the particles of the dispersion composition can also be made very uniform. Furthermore, the dispersion state can be made extremely stable. As meaning for confirming the inclusion state, the ink composition is subjected to Energy-filtered transmission electron microscopy (EFTEM) observation using a cryotransfer system to observe spherical micelles, and the sample is subjected to elementary analysis with electron energy loss spectroscopy (EELS) to confirm the inclusion of the coloring material. Further, if a release of functional substances can be confirmed under micelle disruption conditions, then the inclusion state can be indirectly confirmed.

The sixth feature of the present invention is a composition comprising any one of the above described polymer compounds. The composition of the present invention preferably contains any one of the above described polymers compounds, a coloring material, a functional substance having a predetermined useful function, and a solvent or dispersion medium. The polymer compound can preferably be used to well disperse the coloring material, the functional substance or the like. It is also possible to use a pigment, metal, herbicide, insecticide, or biological material such as a medicine. In addition, the above polymers of the present invention may also be used as good water-soluble polymer compounds. Further, since the polymers can also be used as adhesives or tacking agents, the polymers do not always need to contain a functional substance.

The functional substance may preferably be used in an amount of 0.1 to 50 mass % based on the total mass of the composition of the present invention. Further, it may also be a soluble substance, and dyes, molecular catalysts, and the like may also be used as the functional substance.

Moreover, the polymer compound is preferably contained in the composition of the present invention in an amount of 0.5 to 98 mass % based on the total mass of the composition.

A preferred example of the composition of the present invention may be a recording material containing a solvent or dispersion medium, a coloring material and the above-mentioned polymer compound. Specific examples of such a recording medium may be a toner composition containing a dispersion medium such as a binder resin, a coloring material and the above-mentioned polymer compound, and an ink composition containing a solvent, a coloring material and the above polymer compound.

An ink composition that is a preferred embodiment of the present invention will be described below.

The content of the above-described polymer compound in the ink composition of the present invention is within the range of 0.1 to 90 mass %, preferably 1 to 80 mass %. When used for ink-jet. printers, the content of the polymer compound is preferably within the range of 1 to 30 mass %.

Next, components other than the above-mentioned polymer compounds contained in the ink composition of the present invention will be described in detail below. Examples of other components include organic solvents, water, water-soluble solvents, coloring materials and additives.

[Organic Solvents]

Examples of the organic solvent include hydrocarbons solvent, aromatic solvents, ether solvents, ketone solvents, ester solvents and amide solvents.

[Water]

As water, ion exchange water, pure water and extra pure water wherein metal ions are eliminated are preferable used in the present invention.

[Aqueous Solvents]

Examples of the aqueous solvent used in the invention include: polyvalent alcohols such as ethylene glycol, diethylene glycol, triethylene glycol, polyethylene glycol, propylene glycol, polypropylene glycol or glycerol; polyvalent alcohol ethers such as ethylene glycol monomethyl ether, ethylene glycol monoethyl ether, ethylene glycol monobutyl ether, diethylene glycol monoethyl ether or diethylene glycol monobutyl ether; and nitrogen-containing solvents such as N-methyl-2-pyrrolidone, substituted pyrrolidone or triethanolamine. In addition, monovalent alcohols such as methanol, ethanol or isopropyl alcohol can also be used to accelerate the drying of an aqueous dispersion on a recording medium.

The total content of the organic solvent, water and aqueous solvent described above is preferably within the range of 20 to 95 mass %, more preferably 30 to 90 mass % based on the total mass of the ink composition of the present invention.

[Coloring Materials]

Coloring materials such as pigments or dyes may be contained in the ink composition of the present invention with pigments being more preferably used.

Specific examples of the pigments and dyes used in the ink composition are as follows.

The pigments may be either organic or inorganic pigments. A black pigment and pigments of three primary colors, cyan, magenta and yellow may preferably be used for the ink. Incidentally, color pigments other than those described above, colorless or pale-color pigments, metallic luster pigments, and the like may also be used. Moreover, pigments which have been newly synthesized for the present invention may also be used.

Examples of commercially available black, cyan, magenta and yellow pigments are shown below.

Examples of the black pigment include, but are not limited to, Raven 1060 (manufactured by Colombian Carbon Co.), MOGUL-L (manufactured by Cabot Corp.), Color Black FW1 (manufactured by Degussa AG) and MA100 (manufactured by Mitsubishi Chemical Corp.)

Examples of the cyan pigment include, but are not limited to, C.I. Pigment Blue-15: 3, C.I. Pigment Blue-15: 4 and C.I. Pigment Blue-16.

Examples of the magenta pigment include, but are not limited to, C.I. Pigment Red-122, C.I. Pigment Red-123 and C.I. Pigment Red-146.

Examples of the yellow pigment include, but are not limited to, C.I. Pigment Yellow-74, C.I. Pigment Yellow-128 and C.I. Pigment Yellow-129.

Moreover, pigments self-dispersible in water may also be used for the composition of the present invention. Such pigments dispersible in water include those of which dispersibility is enhanced utilizing a steric hindrance effect of a polymer adsorbed onto the surface thereof, or an electrostatic repulsion. Examples of such pigments that are commercially available include CAB-0-JET200, CAB-0-JET300 (both manufactured by Cabot Corp.), and Microjet Black CW-1 (manufactured by Orient Chemical Corp.).

The pigments used for the ink composition of the present invention are preferably contained in the amount of 0.1 to 50 mass % based on the total mass of the ink composition. If the content of pigment is less than 0.1 mass %, a sufficient image density cannot be obtained. In contrast, if the content of the pigment is more than 50 mass %, the fixation property of an image may be lowered. The content of the pigment is more preferably within the range of 0.5 to 30 mass %.

Furthermore, the dyes may also be used for the ink composition of the present invention. Direct dyes, acid dyes, basic dyes, reactive dyes, water-soluble dyes for food pigments, insoluble pigments as disperse dye, and fat-soluble dyes can be used, which will be described below.

Examples of the water-soluble dyes include direct dyes such as C.I. Direct Black -17, -62 and -154, C.I. Direct Yellow -12, -87 and -142, C.I. Direct Red -1, -62 and -243, C.I. Direct Blue -6, -78 and -199, C.I. Direct Orange -34 and -60, C.I. Direct Violet -47 and -48,-C.I. Direct Brown -109, and C.I. Direct Green -59;

acid dyes such as C.I. Acid Black -2, -52 and -208, C.I. Acid Yellow -11, -29 and -71, C.I. Acid Red -1, -52 and -317, C.I. Acid Blue -9, -93 and -254, C.I. Acid Orange -7 and -19, and C.I. Acid Violet -49;

reactive dyes such as C.I. Reactive Black -1, -23 and -39, C.I. Reactive Yellow -2, -77 and -163, C.I. Reactive Red -3, -111 and -221, C.I. Reactive Blue -2, -101 and -217, C.I. Reactive Orange -5, -74 and -99, C.I. Reactive Violet -1, -24 and -38, C.I. Reactive Green -5, -15 and -23, and C.I. Reactive Brown -2, -18 and -33; and other dyes such as C.I. Basic Black -2, C.I. Basic Red -1, -12 and -27, C.I. Basic Blue -1 and -24, C.I. Basic Violet -7, -14 and -27, C.I. Food Black -1 and -2.

Examples of the fat-soluble dyes include the following commercially available products for each color.

Examples of the black fat-soluble dye include C.I. Solvent Black -3, -22: 1 and -50, but not limited thereto.

Examples of the yellow fat-soluble dye include C.I. Solvent Yellow -1, -25: 1 and -172, but not limited thereto.

Examples of the orange fat-soluble dye include C.I. Solvent Orange -1, -40: 1 and -99, but not limited thereto.

Examples of the red fat-soluble dye include C.I. Solvent Red -1, -111 and -229, but not limited thereto.

Examples of the violet fat-soluble dye include C.I. Solvent Violet -2, -11 and -47, but not limited thereto.

Examples of the blue fat-soluble dye include C.I. Solvent Blue -2, -43 and -134, but not limited thereto.

Examples of the green fat-soluble dye include C.I. Solvent Green -1, -20 and -33, but not limited thereto.

Examples of the brown fat-soluble dye include C.I. Solvent Brown -1, -12 and -58, but not limited thereto.

The above-described examples of the coloring materials are preferable for the ink of the present invention, but coloring materials used for the ink composition of the present invention are not particularly limited to the above-described coloring materials. The dye used for the ink composition of the present invention is preferably contained in the amount of 0.1 to 50 mass % based on the total mass of the ink.

[Additives]

Various additives or auxiliary agents can be added as needed to the composition of the present invention. One of such additives is a dispersion stabilizer, which stably disperses a pigment in a solvent. The composition of the present invention comprises a polymer having a polyvinyl ether structure, so that it has a function to disperse a granular solid such as a pigment. When dispersion is insufficient, however, other dispersion stabilizers may be added.

As other dispersion stabilizers, resins having both hydrophilic and hydrophobic parts, or surfactants can be used. A copolymer consisting of a hydrophilic monomer and a hydrophobic monomer is an example of such a resin having both hydrophilic and hydrophobic moieties.

Examples of such a hydrophilic monomer include acrylic acid, methacrylic acid, maleic acid, fumaric acid, the above described carboxylic acid monoesters, vinylsulfonic acid, styrenesulfonic acid, vinyl alcohol, acrylamide and methacryloxyethyl phosphate. Examples of such a hydrophobic monomer include styrene, styrene derivatives such as $\alpha$-methylstyrene, vinylcyclohexane, vinylnaphthalene derivatives, acrylic acid esters and methacrylic acid esters. Copolymers with various structures, such as a random copolymer, block copolymer or graft copolymer, may be used. Naturally, hydrophilic and hydrophobic monomers used herein are not limited to the above-described examples.

Examples of the surfactant to be used include anionic, nonionic, cationic and amphoteric surfactants. Examples of the anionic surfactant include a fatty acid salt, alkyl sulfate, alkylaryl sulfonate, alkyldiaryl ether disulfonate, dialkyl sulfosuccinate, alkyl phosphate, naphthalenesulfonic acid formalin condensate, alkyl polyoxyethylene phosphate, and glycerol borate fatty acid ester. Examples of the nonionic surfactant include polyoxyethylene alkyl ether, a polyoxyethyleneoxy propylene block copolymer, sorbitan fatty acid ester, glycerin fatty acid ester, polyoxyethylene fatty acid ester, polyoxyethylene alkylamine, a fluorine-based surfactant, and a silicon-based surfactant. Examples of the cationic surfactant include an alkylamine salt, a quaternary ammonium salt, an alkylpyridinium salt, and an alkylimidazolium salt. Examples of the amphoteric surfactant include alkyl betaine, alkylamine oxide and phosphatidylcholine. In addition, surfactants are also not limited to the above examples.

Further, an aqueous solvent may be added, as needed, to the composition of the present invention. In particular, when the composition is used for an ink for ink jetting, such an aqueous solvent is used also to prevent drying of the ink at a nozzle portion and consolidation of the ink. The aqueous solvent can be used singularly or in combination. The above listed examples of aqueous solvents can be used as such. In the case of an ink, the content of the aqueous solvent is within the range of 0.1 to 60 mass %, preferably 1 to 40 mass % based on the total mass of the ink.

When the composition is used for ink, examples of other additives include a pH adjuster used to stabilize the ink and to achieve stable piping of the ink in a recording apparatus; a penetrant used to promote the penetration of the ink into a recording medium so as to hasten apparent drying; a fungicide used to prevent generation of molds in the ink; a chelating agent used to block metal ions in the ink so as to prevent deposition of the metal at a nozzle portion or deposition of insoluble matters in the ink; an antifoaming agent used to prevent the generation of bubbles during the circulation or movement of a recording liquid or the production of the recording liquid; an antioxidant; a fungicide; a viscosity adjuster; an electric conductive agent; and an ultraviolet absorber.

To prepare the ink composition of the present invention, the above constituents are mixed, and they are uniformly dissolved or dispersed. For example, a plurality of components are mixed, and the mixture is grounded and dispersed with a sand mill, ball mill, homogenizer or nanomiser to prepare an ink mother liquid, and solvents or additives are added thereto to adjust physical properties, thereby producing the ink composition of the present invention.

Subsequently, the toner composition of the present invention will be described below. Specifically, the toner composition comprises a dispersion medium such as a binder resin, a coloring material and the above-described polymer compound.

The content of the polymer compound in the toner composition of the present invention is generally within the range of 0.1 to 95 mass %, and preferably within the range of 0.5 to 80 mass %.

Moreover, the polymer compound of the present invention can be used alone as a binder resin, or it can also be used in combination with another binder resin such as a styrene acrylic resin or polyester resin.

Subsequently, components other than the polymer compound to be contained in the toner composition of the present invention will be described in detail. Examples of the other components include a binder resin, a coloring material (pigment or dye), a charge controlling agent, a mold release agent, an external additive and a magnetic particle.

(Addition of Other Components to Toner Composition)

Examples of the binder resin include a styrene acrylic copolymer, polyester and polycarbonate. The content of such a binder resin is preferably 10 to 99 mass %. As the coloring material the pigments or dyes described for the above ink composition can be used. The content of such a coloring material is 0.1 to 50 mass %. Examples of the charge controlling agent include a metal-azo complex, a triphenylmethane dye, nigrosine and an ammonium salt. The content of the antistatic agent is 0.1 to 30 mass %. Examples of the mold release agent include a synthetic wax and a natural wax. Examples of the external additive include inorganic fine particles such as silica, alumina or titania, and resin fine particles such as polyvinylidene fluoride (PVDF) or polytetrafluoroethylene. Examples of the magnetic particle include magnetite, hematite and ferrite. The toner composition can function even when it does not contain all the above components, and may further contain components other than those described above.

In order to prepare the toner composition of the present invention, for example, the above-described components are mixed, melted and kneaded, so as to obtain a homogeneous mixture, which mixture is then grounded with a speed mill or jet mill, and the obtained particles are classified by size, so as to obtain toner with a desired size. The external additive may be added to the toner, and the mixture is mixed with a mixer, so as to obtain the toner composition of the present invention.

Next, the image formation method, liquid application method, and image formation apparatus that use the composition of the present invention will be described.

[Image Formation Method, Liquid Application Method, and Apparatus]

The composition of the present invention can be used for various types of image formation methods and apparatuses, such as various printing,methods, ink-jet methods or electrophotography. An image can be printed by the above image formation method using the above apparatus. Further, when using the liquid composition, a fine pattern can be formed by the ink-jet method, or such a liquid composition can be used for the liquid application method including administration of a medicine or the like.

The image formation method of the present invention is a method of forming an excellent image using the composition of the present invention. The image formation method of the present invention is preferably a method of discharging the ink composition of the present invention from an ink discharge unit to deposit it on a recording medium, thereby effecting recording. As the image formation method, the ink-jet method is preferably used which imparts a thermal energy to the ink to discharge the ink.

As the ink-jet printer using the ink-jet ink composition of the present invention, there are used various ink-jet recording apparatuses such as a piezo ink-jet system recording apparatus using a piezoelectric element, or a bubble jet (registered trademark) system in which a thermal energy is imparted to an ink to generate a bubble, thus performing recording.

The overview of the ink-jet recording apparatus will be explained below, referring to. FIG. 1. However, FIG. 1 is only an example of the structure, and it is not intended to limit the present invention.

FIG. 1 is a block diagram showing a structure of the ink-jet recording apparatus.

FIG. 1 shows a case where a head is moved to perform recording on a recording medium. In FIG. 1, an X direction drive motor 56 and a Y direction drive motor 58, which drive a head 70 in X and Y directions, are connected to a CPU 50 for controlling the entire movement of the recording apparatus via an X motor drive circuit 52 and a Y motor drive circuit 54, respectively. In accordance with instructions from the CPU, the X direction drive motor 56 and the Y direction motor drive motor 58 are driven via the X motor drive circuit 52 and the Y motor drive circuit 54, so that the location of the head 70 on the recording medium is determined.

As shown in FIG. 1, not only the X direction drive motor 56 and the Y direction motor drive motor 58, but also a head drive circuit 60 is provided to be connected to the head 70. The CPU 50 controls the head drive circuit 60 to drive the head 70, that is, to discharge the ink-jet ink. Moreover, an X encoder 62 and a Y encoder 64, which detect the location of the head, are connected to the CPU 50, and the information regarding the location of the head is inputted in the encoders. Furthermore, a control program is also inputted in a program memory 66. The CPU 50 moves the head 70, based on the control program and the information regarding the location from the X encoder 62 and the Y encoder 64, so that the head is positioned at a desired location on the recording medium and the ink-jet ink is then discharged. Thus, a desired image can be formed on the recording medium. Further, in the case of an image recording apparatus that can be equipped with multiple ink-jet inks, the above operation is carried out for each ink-jet ink a given number of times, so that a desired image can be formed on the recording medium.

Further, after the ink-jet ink has been discharged, the head 70 may be moved, as needed, to a location where an ink removal means (not shown in the figure) for removing an excess ink attached to the head is provided, and the head 70 may be cleaned by wiping or the like. As specific cleaning methods, the conventional cleaning methods can be used as such.

After completion of the formation of the image, the recording medium on which the image has been formed is replaced with a new recording medium by a carrying mechanism for recording media, which is not shown in the figure.

It is to be noted that in the present invention, the above-described embodiment can be changed or modified without departing from the sprit or scope of the invention. For example; although the head 70 is moved in the X-Y axes directions in the above explanation, the head 70 may be moved only in the X axis direction (or Y axis direction) while the recording medium may be moved in the Y axis direction (or X axis direction), and thus, the head and the recording medium may be moved relative to each other to form an image.

The present invention especially exhibits excellent effects when applied to a head that has a means (for example, an electrothermal transducer, laser beam, etc.) for generating a thermal energy, which is utilized to discharge an ink-jet ink, and discharges the ink-jet ink using the thermal energy. Such an ink-jet system enables formation of a finer image. By using the ink-jet ink composition of the present invention, a more excellent image can be printed.

As the representative structure or principle of the apparatus having the above heat energy-generating means, basic principles disclosed in U.S. Pat. Nos. 4,723,129 and 4,740,796 are preferably used. This system can be applied to both the so-called on-demand type and continuous type. It is particularly effective to apply this system to the on-demand type. This is because, in the case of the on-demand type, at least one driving signal, which corresponds to a discharging information and gives a rapid increase in temperature that exceeds nuclear boiling, is applied to an electrothermal transducer located corresponding to a liquid path that retains liquid, so that a thermal energy is generated from the electrothermal transducer, thereby causing film boiling on a heat acting surface of the head, whereby an air bubble can be formed in the liquid in a one-to-one correspondence with the driving signal. By the growth and shrinkage of the air bubble, liquid is discharge via a discharging opening to form at least one ink droplet. If this driving signal is of a pulse-shape, the growth and shrinkage of a air bubble is carried out rapidly and appropriately, so that liquid discharge that is particularly excellent in signal-responsibility can be achieved, which is more preferable. As such a pulse-type driving signal, those described in U.S. Pat. Nos. 4,463,359 and 4,345,262 are appropriate. In addition, with regard to the above-described rate of raise in the temperature of the heat acting surface, when the conditions described in U.S. Pat. No. 4,313,124 are adopted, more excellent ink discharge can be carried out.

With regard to the structure of the head, not only the combined structure (a linear liquid path or right angle liquid path) consisting of a discharge port, a liquid path and an electrothermal transducer that is described in each of the above specifications, but the structure that a heat acting unit is located in a bending region, described in U.S. Pat. Nos. 4,558,333 and 4,459,600, are also included in the present invention. In addition, the structure in which multiple electrothermal transducers use a common slit as a discharging unit, described in Japanese Patent Application Laid-Open No. S59-123670, or the structure in which an opening port for absorbing the pressure wave of thermal energy corresponds to the discharging unit, described in Japanese Patent Application Laid-Open No. S59-138461, is also effective for the present invention. This is to say, regardless of the form of the head, an ink-jet ink can be reliably and efficiently discharged according to the present invention.

Moreover, the present invention can also be effectively applied to a full line-type head having a length corresponding to the maximum width of a recording medium in the image formation apparatus of the present invention. The structure of such a head may be either a structure satisfying the above length by a combination of multiple heads, or structure as a single-piece head.

In addition, the present invention is also effective for a serial type head, a head fixed to the main body of an apparatus, or an exchangeable chip type head which is equipped in the main body of an apparatus, thereby enabling electric connection with the main body or ink supply from the main body.

Furthermore, the apparatus of the present invention may further comprise a droplet removal means. When such a means is added to the apparatus, further excellent discharging effects can be realized.

Still further, preliminary assisting means is preferably added to the apparatus of the present invention to further stabilize the effects of the present invention. Specific examples of such assisting means include a capping means for the head, a pressurizing or sucking means, a preliminary heating means for performing-heating using an electrothermal transducer, other heating elements or a combination thereof, and preliminary discharging means for performing discharge other than the discharge of an ink.

The above film boiling system is the most effective for the present invention.

In the apparatus of the present invention, the amount of the ink-jet ink discharged from each discharging port of the discharge head is preferably within the range of 0.1 to 100 picolitre.

Still further, the ink composition of the present invention can also be used for an indirect recording apparatus using a recording system wherein an ink is printed on an intermediate transfer member and then transferred on a recording medium such as a paper sheet. Further, the ink composition of the present invention can also be applied to an apparatus using a direct recording system wherein such an intermediate transfer member is used.

EXAMPLES

The present invention will be described in detail in the following examples. However, these examples are not intended to limit the scope of the present invention.

Example 1

Figure 2:
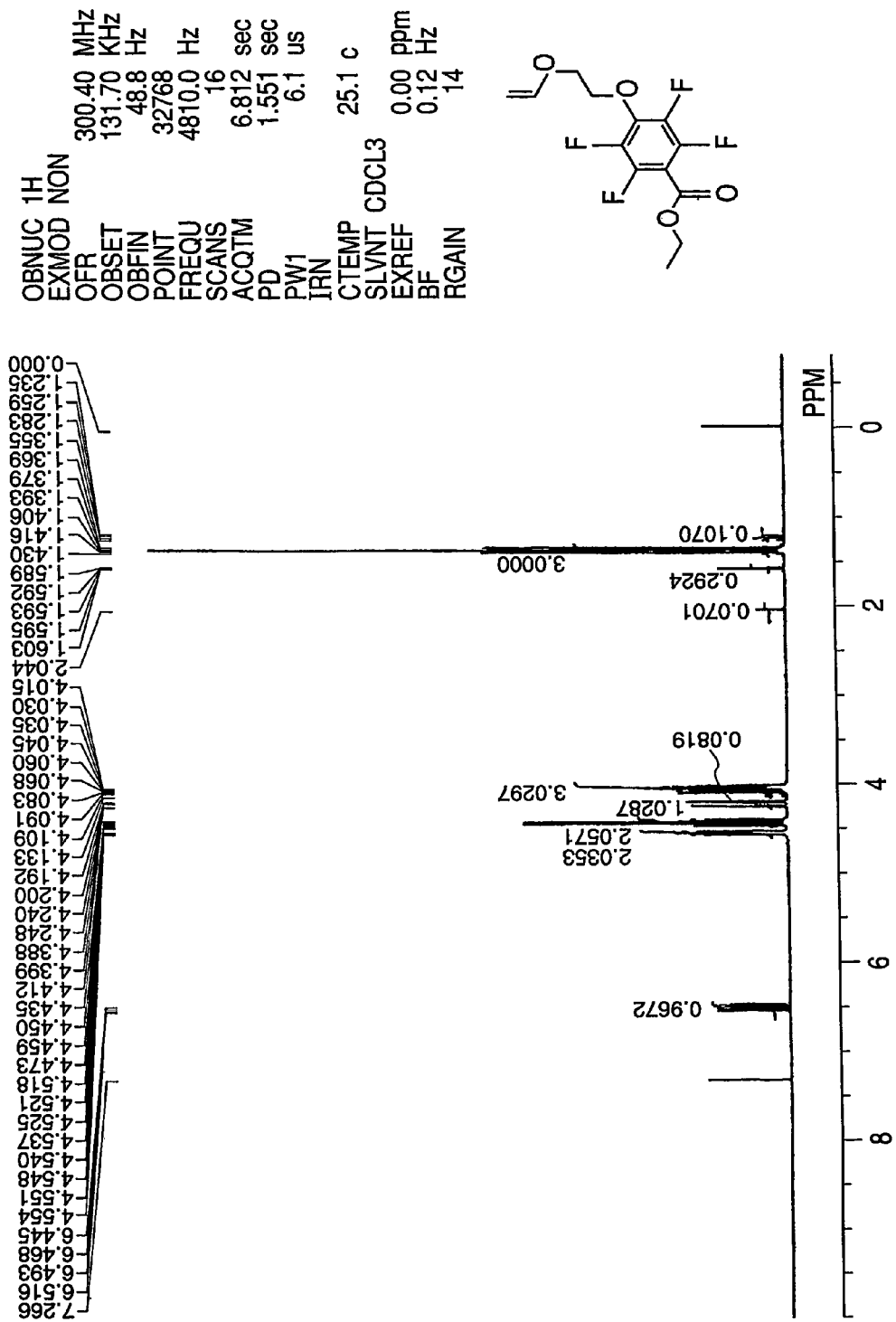
FIG. 2 is a view showing NMR of the polymeric compound of Example 1 of the present invention.

Synthesis of $CH_2=CHOCH_2CH_2OPh(4F)COOC_2H_5$ 25 parts by mass of pentafluorobenzoic acid ethyl ester and 21.6 parts by mass of $NaNO_2$ were mixed in 200 parts by mass of DMSO, and the mixture was heated. After the mixture was stirred at 50° C. for 2 hours, it was cooled to room temperature, and 520 parts by mass of ice water was added thereto. Concentrated hydrochloric acid was added to the mixture to adjust pH to 2, and the mixture was then heated to 100° C. followed by stirring for 30 minutes. The mixture was cooled to room temperature followed by extraction with ether. Organic layers were washed with water and dried with anhydrous magnesium sulfate. The solvent was removed, and the obtained residue was washed with hexane to obtain 4-hydroxy-2,3,5,6-tetrafluorobenzoic acid ethyl ester. 200 parts by mass of the obtained 4-hydroxy-2,3,5,6-tetrafluorobenzoic acid ethyl ester was dissolved in 500 parts by mass of DMF, and an equivalent amount of NaH was gradually added thereto followed by stirring for 1 hour. 20 parts by mass of tetrabutylammonium iodide was added thereto, 180 parts by mass of 2-chloroethyl vinyl ether was then added thereto, and the thus obtained mixture was stirred at 100° C. for 10 hours. After cooling to room temperature, the reaction solution was added to 4,600 parts by mass of ice water followed by extraction with ethyl acetate. Organic layers were washed with water and dried with anhydrous magnesium sulfate. The solvent was removed, and the residue was subjected to silica gel column chromatography to obtain the objective polymeric compound. The NMR of the thus obtained polymeric compound is shown in FIG. 2.

Example 2

Synthesis of Polymer 0.1 mol of the polymeric compound obtained in Example 1, 0.001 mol of water and 0.005 mol of ethyl aluminum dichloride were subjected to cationic polymerization in anhydrous toluene.

After 20 hours the reaction was completed, and methylene chloride and water were added to the reaction product, and the mixture was washed with water and then with diluted hydrochloric acid, and further washed with alkali. Thereafter, the thus washed product was dried with anhydrous sodium sulfate, and the solvent was removed to obtain a high molecular compound (polymer). The number-average molecular weight of the polymer measured by the size exclusion chromatography was 2,500.

Example 3

Synthesis of $CH_2=CHO(CH_2CH_2O)_2Ph(4F)COOC_2H_5$

The synthesis was carried out in the same manner as in Example 1 with the exception that $CH_2=CHOCH_2CH_2OCH_2CH_2OTs$ (wherein Ts represents a tosyl group) was used instead of 2-chloroethyl vinyl ether of Example 1 to obtain the objective polymeric compound.

Example 4

Using each polymeric compound obtained in Example 3, the polymerization was carried out in the same manner as in Example 2 to obtain a polymer compound. The number-average molecular weight of the polymer compound measured by the size exclusion chromatography was 1,800.

Example 5

The high molecular compound (polymer) synthesized in Example 2 was mixed with a 5N aqueous sodium hydroxide solution, and the mixture was stirred at room temperature (23° C.) for 40 hours, so that ester was hydrolyzed. The solution was neutralized with 5N hydrochloric acid, extracted with methylene chloride, and dried. Thereafter, the solvent was removed to obtain a free carboxylic acid polymer. The obtained polymer was neutralized with an equivalent amount of 1N sodium hydroxide, and water was than removed to obtain a sodium carboxylate polymer.

Example 6

2 parts by mass of pigment (product name: Mogul L, manufactured by Cabot Corp.), 3 parts by mass of the sodium carboxylate polymer of Example 5, and 25 parts by mass of diethylene glycol were added to 177 parts by mass of ion exchange water, followed by dispersion with an ultrasonic homogenizer. The dispersion solution was subjected to pressure filtration using 1 μm filter to prepare an ink composition. The pigment had good dispersibility.

Example 7

Synthesis of $CH_2=CHOCH_2CH_2OPh(2F)COOC_2H_5$ wherein two fluorine atoms are substituted at positions 3 and 5 of benzoic acid The objective compound was synthesized using HOPh(2F)$COOC_2H_5$ in the same manner as in Example 1. Using the obtained compound, a polymer was synthesized in the same manner as in Example 2.

Example 8

Using the ink composition prepared in Example 6, ink-jet recording was carried out. An ink tank of a bubble jet (registered trademark) printer (product name: BJJ-800J) manufactured by Canon Inc. was filled with the ink composition of Example 6. Using this ink-jet printer, recording was carried out on a plain paper sheet. As a result, clear black printing was achieved.

Example 9

Using the free carboxylic acid polymer that is a precursor of the sodium carboxylate polymer obtained in Example 5, a toner composition was produced by the following method.

100 parts by mass of polyester resin (bisphenol A, terephthalic acid, n-dodecenylsuccinic acid, trimellitic acid and diethylene glycol were synthesized at a molar ratio of 20:38:10:5:27), 70 parts by mass of magnetite ($Fe_3O_4$), 3 parts by mass of the above described free carboxylic acid polymer, 2 parts by mass of triphenylmethane dye, and 3 parts by mass of low molecular-weight polypropylene were preliminarily mixed, and the obtained mixture was melted and kneaded with a ruder. After cooling the resultant product, it was roughly grounded with a speed mill, and then finely grounded with a jet mill. Thereafter, the particles were classified using a zigzag separator to obtain toner having a volume mean diameter of 11 μm.

0.4 part by mass of positively-charged hydrophobic dry silica treated with amino-modified silicon oil (having viscosity at 25° C. of 100 cp and amine equivalence of 800) and 0.2 part by mass of spherical PVDF particles having a mean particle size of 0.2 μm were added to 100 parts by mass of the above obtained toner. Thereafter, the mixture was blended with a Henschel mixer, so as to obtain a positively charged toner composition. Using this toner composition, printing was carried out with a printer NP-3525 manufactured by Canon Inc. As a result, clear printing was achieved.

Example 10

Synthesis of Block Polymer

Synthesis of a diblock polymer consisting of isobutyl ether, $CH_2=CHOCH_2CH_2OPhPh$:(IBVE-r-VEEtPhPH: A block), and 4-(2-vinyloxy)ethoxy-2,3,5,6-tetrafluorobenzoic acid ethyl (VEOEtPh(4F)COOEt: B block)

The inside of a glass container equipped with a three-way cock was subjected to nitrogen substitution, and adsorbed water was eliminated by heating to 250° C. under a nitrogen gas atmosphere. The system was returned to room temperature, and thereafter, 6 mmol (millimole) of IBVE, 6 mmol of VEEtPhPh, 16 mmol of ethyl acetate, 0.1 mmol of 1-isobutoxyethyl acetate, and 11 ml of toluene were added to the reaction system. Thereafter, the reaction system was cooled. When the temperature in the system was reached 0° C., 0.2 mmol of ethylaluminum sesquichloride (an equimolar mixture consisting of diethylaluminum chloride and ethylaluminum dichloride) was added to the reaction system, so as to initiate polymerization. Molecular weight was monitored by molecular sieve chromatography (GPC) in a time-division manner, and thus, completion of the polymerization of the A block was confirmed.

Subsequently, 10 mmol of the B block monomer was added thereto, and the polymerization was continued. 24 hours later, the polymerization reaction was terminated. The polymerization reaction was terminated by adding 0.3% by mass of ammonia/methanol aqueous solution to the system. The reaction mixture solution was diluted with dichloromethane, and the diluted solution was washed with 0.6 M hydrochloric acid 3 times and then with distilled water 3 times. The obtained organic layers were concentrated and exsiccated with an evaporator, and the obtained vacuum-dried product was repeatedly dialyzed using a cellulose semipermeable membrane in a methanol solvent to eliminate monomeric compounds, so as to obtain a diblock polymer of interest. The compound was identified by NMR and GPC. As a result, Mn=14,600 and Mw/Mn=1.32. The polymerization ratio (=compositional ratio) was A:B=100:10. The polymerization ratio of two types of monomers was 1:1 in the A block.

Thereafter, the thus obtained block polymer was hydrolyzed in a mixed solution consisting of dimethylformamide and sodium hydroxide water. Thus, the B block components were hydrolyzed, so as to obtain a diblock polymer that was converted into a sodium salt. The compound was identified by NMR and GPC.

Thereafter, the compound was neutralized with 0.1 N hydrochloric acid in a water dispersion solution, so as to obtain a diblock polymer wherein B components became free carboxylic acids. The compound was identified by NMR and GPC.

[pKa Measurement of B Block]

3.0 mmol of an aliquot was picked up at a monomer unit of the B block components from the carboxylic acid-type block polymer obtained in Example 10. Then, distilled water was added thereto to obtain 50 g of aqueous solution in total. A 0.1N aqueous sodium hydroxide solution was added to the obtained aqueous solution, and the mixture was measured by potentiometric titration to obtain pKa. As a result, pKa=2.2. The titration was carried out using an automatic titrater "COM-555" (manufactured by Hiranuma Sangyo Co., Ltd.)

Example 11

15 parts by mass of the carboxylic acid salt-type block polymer obtained in Example 10 and 7 parts by mass of Oil Blue N (C.I. Solvent Blue-14 manufactured by Aldridge) were codissolved in 150 parts by mass of dimethylformamide. The resultant product was converted into an aqueous phase using 400 parts by mass of distilled water, so as to obtain an ink composition. Although the obtained ink composition was left for 10 days, the Oil Blue was neither separated nor deposited.

Example 12

The printing head of an ink-jet printer (product name: BJF800, manufactured by Canon Inc.) was filled with the ink prepared in Example 11, and recording was carried out. 1 minute after the recording, the printed portion was strongly scratched 3 times with a line marker, but tailing of blue color did not appear at all. Thus, it was found that the ink has extremely good fixability.

Comparative Example 1

2 parts by mass of black self-dispersing pigment (product name: CAB-0-JET300, manufactured by Cabot Corp.), 0.5 part by mass of surfactant (Nonion E-230 manufactured by NOF Corp.), 5 parts by mass of ethylene glycol, and 92.5 parts by mass of ion exchange water were mixed to prepare an ink composition. Using the ink composition, recording was carried out in the same manner as in Example 3. 1 minute after the recording, the printed portion was strongly scratched once with a line marker. As a result, tailing of black color was observed.

Example 13

Synthesis of Block Polymer

Synthesis of a triblock polymer consisting of isobutyl vinyl ether (IBVE: A block), 2-methoxyethyl vinyl ether (MOVE: B block), and 4-(2-vinyloxy)ethoxy-2,3,5,6-tetrafluorobenzoic acid ethyl (VEOEtPh(4F)COOEt: C block)

The inside of a glass container equipped with a three-way cock-was subjected to nitrogen substitution, and adsorbed water was eliminated by heating to 250° C. under a nitrogen gas atmosphere. The system was returned to room temperature, and thereafter, 12 mmol (millimole) of IBVE, 16 mmol of ethyl acetate, 0.05 mmol of 1-isobutoxyethyl acetate, and 11 ml of toluene were added to the reaction system. Thereafter, the reaction system was cooled. When the temperature in the system was reached 0° C., 0.2 mmol of ethylaluminum sesquichloride (an equimolar mixture consisting of diethylaluminum chloride and ethylaluminum dichloride) was added to the reaction system to initiate polymerization. Molecular weight was monitored by molecular sieve chromatography (GPC) in a time-division manner, and thus, completion of the polymerization of the A block was confirmed.

Subsequently, 12 mmol of MOVE as the B block was added thereto, and the polymerization was continued. Completion of the polymerization of the B block was confirmed by monitoring using GPC. Thereafter, 10 mmol of the C block monomer was added thereto, and the polymerization was continued. 24 hours later, the polymerization reaction was terminated. The polymerization reaction was terminated by adding 0.3% by mass of ammonia/methanol aqueous solution to the system. The reaction mixture solution was diluted with dichloromethane, and the diluted solution was washed with 0.6 M hydrochloric acid 3 times and then with distilled water 3 times. The obtained organic layers were concentrated and exsiccated with an evaporator, and the obtained vacuum-dried product was repeatedly dialyzed using a cellulose semipermeable membrane in a methanol solvent to eliminate monomeric compounds to obtain a triblock polymer of interest. The compound was identified by NMR and GPC. As a result, Mn=40,685 and Mw/Mn=1.41. The polymerization ratio was A:B:C=200:200:30.

Thereafter, the thus obtained block polymer was hydrolyzed in a mixed solution consisting of dimethylformamide and sodium hydroxide water. Thus, the C block components were hydrolyzed, so as to obtain a triblock polymer that was converted into a sodium salt. The compound was identified by NMR and GPC.

Thereafter, the compound was neutralized with 0.1 N hydrochloric acid in a water dispersion solution to obtain a triblock polymer wherein C components became free carboxylic acids. The compound was identified by NMR and GPC.

Example 14

15 parts by mass of the carboxylic acid salt-type block polymer obtained in Example 13 and 7 parts by mass of Oil Blue N (C.I. Solvent Blue-14 manufactured by Aldridge) were codissolved in 150 parts by mass of dimethylformamide. The resultant product was converted into an aqueous phase using 400 parts by mass of distilled water, so as to obtain an ink composition. Although the obtained ink composition was left for 10 days, the Oil Blue was neither separated nor deposited.

In addition, encapsulation of the coloring material in the block polymer was confirmed by EF-TEM observation with a cryotransfer device and elementary analysis with EELS, as stated above. Moreover, 5 samples were prepared by applying the ink on plain papers, and they were then subjected to a light resistance test under the outside light for approximately 2 months, using a light resistance tester Suntest CPS+ manufacture by Toyo Seiki). As a result, it was found that all the samples kept an optical density of 90% or more.

Comparative Example 2

The Oil Blue N (C.I. Solvent Blue-14 manufactured by Aldridge) used in Example 14 was dissolved in THF. In the same manner as in Example 14, 5 samples were prepared by applying the ink on plain papers, and they were then subjected to a light resistance test under the outside light for approximately 2 months, using a light resistance tester Suntest CPS+ manufacture by Toyo Seiki). As a result, it was found that all the samples had an optical density of less than 75%.

Example 15

The printing head of an ink-jet printer (product name: BJF800, manufactured by Canon Inc.) was filled with the ink prepared in Example 14, and recording was carried out. 1 minute after the recording, the printed portion was strongly scratched 3 times with a line marker, but tailing of blue color did not appear at all. Thus, it was found that the ink has extremely good fixability.

Example 16

Water dispersion solutions were prepared, each of which contained 15% by weight of the carboxylic acid ester-type triblock polymer or 15% by weight of the carboxylic acid salt-type triblock polymer that were obtained in Example 13. Each solution was observed with a polarizing microscope. As a result, completely different textures were observed from the solutions, and thus, formation of different structures was observed.

A water dispersion solution containing 15% by weight of the carboxylic acid ester-type diblock polymer obtained in Example 10 was mixed with a water dispersion solution containing 15% by weight of the carboxylic acid ester-type triblock polymer at a weight ratio of 1:2, and the obtained mixture was observed with a polarizing microscope. As a result, it was found that a texture similar to the texture of the carboxylic acid ester-type triblock polymer was observed but that the intensity of transmitted light was reduced. It is therefore considered that there was no change in the basic structure but that a structure with reduced order parameter was formed.

Example 17

A triblock polymer was synthesized in the same manner as in the case of the carboxylic acid ester-type triblock polymer of Example 13 with the exception that 4-(2-vinyloxy)ethoxy-2,3,4,5,6-polyfluorobenzene was used instead of 4-(2-vinyloxy)ethoxy-2,3,5,6-tetrafluorobenzoic acid ethyl. A water dispersion solution containing 15% by weight of the polymer was prepared, and it was then observed with a polarizing microscope. As a result, a texture similar to the texture of the carboxylic acid ester-type triblock polymer of Example 16, and formation of a similar structure was observed.

The invention claimed is:

1. An amphiphilic block polymer comprising:
   (a) a hydrophilic block segment having a repeating unit structure represented by the general formula (4):

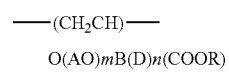

wherein:
   A represents a linear alkylene group of 1 to 15 carbon atoms;
   m represents 0 or 1;
   B represents a single bond or an alkylene group of 1 to 20 carbon atoms;
   each D represents independently an aromatic ring structure in which at least one hydrogen atom attached to the ring is displaced by a fluorine atom;
   n represents an integer of 1 to 10; and
   R represents an alkyl group or an aromatic ring structure, and
   (b) a hydrophobic block segment.

2. The amphiphilic block polymer according to claim 1, further comprising another hydrophilic block segment.

3. The amphiphilic block polymer according to claim 1, wherein four hydrogen atoms attached to the aromatic ring structure represented by D in the general formula (4) are each displaced by fluorine atoms.

4. The amphiphilic block polymer according to claim 1, wherein the hydrophobic block segment has a repeating unit structure represented by the general formula (8):

wherein:
   $R^1$ is selected from the group consisting of a linear, branched, or cyclic alkyl groups of 1 to 18 carbon atoms, -Ph, -Pyr, -Ph-Ph, -Ph-Pyr, —(CH($R^5$)—CH($R^6$)—O)

$_p$—R$^7$, and —(CH$_2$)$_m$—(O)$_n$—R$^7$, and hydrogen atom(s) in the aromatic ring may be replaced by linear or branched alkyl group(s) of 1 to 4 carbon atoms, and carbon atom(s) in the aromatic ring may be replaced by nitrogen atom(s), wherein:

p represents an integer of 1 to 18;

m represents an integer of 1 to 36;

n represents 0 or 1;

each of R$^5$ and R$^6$ represents independently a hydrogen atom or —CH$_3$; and R$^7$ is selected from the group consisting of a hydrogen atom, a linear, branched, or cyclic alkyl group of 1 to 18 carbon atoms, -Ph, -Pyr, -Ph-Ph, -Ph-Pyr, —CHO, —CH$_2$CHO, —CO—CH=CH$_2$, —CO—C(CH$_3$)=CH$_2$ and CH$_2$COOR$_8$, and when R$^7$ is other than a hydrogen atom, hydrogen atom(s) attached to carbon atom(s) in R$^7$ may be replaced by a linear or branched alkyl group of 1 to 4 carbon atoms, —F, —Cl, or —Br, and carbon atom(s) in the aromatic ring may be replaced by nitrogen atom(s), wherein:

R$^8$ represents a hydrogen atom or an alkyl group of 1 to 5 carbon atoms;

Ph represents a phenyl group; and

Pyr represents a pyridyl group.

* * * * *